United States Patent
Stuart et al.

(10) Patent No.: US 6,444,430 B1
(45) Date of Patent: *Sep. 3, 2002

(54) NDR2-RELATED PROTEINS

(75) Inventors: Susan G. Stuart, Montara; Janice Au-Young, Brisbane; Jennifer L. Hillman, Mountain View; Purvi Shah, San Jose; Henry Yue, Sunnyvale, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/812,484

(22) Filed: Mar. 19, 2001

Related U.S. Application Data

(63) Continuation-in-part of application No. 09/232,160, filed on Jan. 15, 1999.

(51) Int. Cl.⁷ .......................... C12Q 1/68; C12P 19/34; C07H 19/00; C07H 21/02; C07H 21/04
(52) U.S. Cl. ................... 435/6; 435/91.1; 536/22.1; 536/23.1; 536/24.31; 536/24.32
(58) Field of Search ................... 435/6, 91.1; 536/22.1, 536/23.1, 24.31, 24.32

(56) References Cited

PUBLICATIONS

Agarwala et al., "Phosphorylation of RTP, and ER Stress–Responsive Cytoplasmic Protein", Biochem Biophys Res Commun 272:641–647 (2000).
Kurdistani et al., "Inhibition of Tumor Cell Growth by RTP/rit 42 and Its Responsiveness to p53 and DNA Damage[1]", Cancer Res 58:4439–4444 (1998).
van Belzen et al., "A Novel Gene Which Is Up–Regulated during Colon Epithelial Cell Differentiation and Down–Regulated in Colorectal Neoplasms", Lab Invest 77:85–92 (1997).
Piquemal et al., "Differential expression of the RTP/Drg 1/Ndr1 gene product in proliferating and growth arrested cells", Biochem Biophys Acta 1450: 364–373 (1999).
Ulrix et al., "The differentiation–related gene 1, Drg1, is markedly upregulated by androgens in LNCaP prostatic adenocarcinoma cells", FEBS Lett 455:23–26 (1999).
Shimono, Okuda, and Kondoh, "N–myc–dependent repression of Ndr1, a gene identified by direct subtraction of whole mouse embryo cDNAs between wild type and N–myc mutant", Mech Dev 83:39–52 (1999).
Grandori et al., "The MYC/MAX/MAD Network and the Transcriptional Control of Cell Behavior", Annu Rev Cell Dev Biol 16:653–699 (2000).
Okuda and Kondoh, "Identification of New Genes Ndr2 and Ndr3 Which Are Related to Ndr1/RTP/Drg 1 but Show Distinct Tissue Specificity and Response to N–myc", Biochem and Biophys Res Commun 266:208–215 (1999).
NCBI, Accession No. AB033921, g6141565, Okuda et al., Dec. 22, 1999.
NCBI, Accession No. D87953, g1596166, Kokame et al., Feb. 7, 1999.

*Primary Examiner*—W. Gary Jones
*Assistant Examiner*—Arun K. Chakrabarti
(74) *Attorney, Agent, or Firm*—Incyte Genomics, Inc.

(57) ABSTRACT

The invention provides cDNA which encode Ndr2-related proteins. It also provides for the use of the cDNAs, fragments, complements, and variants thereof and of the encoded proteins, portions thereof and antibodies thereto for diagnosis and treatment of cancer, particularly cancers of the intestine, breast, uterus, liver, brain, and kidney. The invention additionally provides expression vectors and host cells for the production of the proteins and a transgenic model system.

14 Claims, 17 Drawing Sheets

```
5'  AGA GCA GGC GTC GGG ACG CAG CAA AGA GAG GAG AGT CAG AAG GAG
        9          18          27          36          45          54

TGA GAA CCC TGA CCC CTA ATC CCA CAT CTG CCA AAT AGG AGC CCA GCC ACC
    63          72          81          90          99          108

ATG GCG GAG CTG CAG GAG GTG CAG ATC ACA GAG AAG CCA CTG TTG CCA GGA
         M   A   E   L   Q   E   V   Q   I   T   E   K   P   L   L   P   G
    117         126         135         144         153         162

CAG ACG CCT GAG GCG AAG GCC AAG GAG GCT GAG TTA GCT GCC CGA ATC CTC CTG GAC
         Q   T   P   E   A   K   A   K   E   A   E   L   A   A   R   I   L   L   D
    171         180         189         198         207         216

CAG GGA CAG ACT CAC TCT GTG GAG ACA CCA TAC GGC TCT GTC ACT TTC ACT GTC
         Q   G   Q   T   H   S   V   E   T   P   Y   G   S   V   T   F   T   V
    225         234         243         252         261         270

CAG ACC CCC AAA CCC AAA CGC CCA GCG ATC CTT ACC TAC CAC GAT GTG GGA
         Q   T   P   K   P   K   R   P   A   I   L   T   Y   H   D   V   G
    279         288         297         306         315         324

TAT GGC
         Y   G
```

FIGURE 1A

| CTC | AAC | TAT | AAA | TCT | TGC | TTC | CAG | CCA | CTG | TTT | CAG | TTC | GAG | GAC | ATG | CAG | GAA |
|---|---|---|---|---|---|---|---|---|---|---|---|---|---|---|---|---|---|
| 333 | | | | | 342 | | | 351 | | | 360 | | | 369 | | | 378 |
| L | N | Y | K | S | C | F | Q | P | L | F | Q | F | E | D | M | Q | E |

| ATC | ATT | CAG | AAC | TTT | GTG | CGG | GTT | CAT | GTG | GAT | CCT | GGA | ATG | GAA | GAG | GGA |
|---|---|---|---|---|---|---|---|---|---|---|---|---|---|---|---|---|
| | 387 | | | | 396 | | | 405 | | | 414 | | | 423 | | 432 |
| I | I | Q | N | F | V | R | V | H | V | D | P | G | M | E | E | G |

| GCC | CCT | GTG | TTC | CCT | TTG | GGA | TAT | CAG | TAC | CCA | TCT | CTG | GAC | CAG | CTT | GCA | GAC |
|---|---|---|---|---|---|---|---|---|---|---|---|---|---|---|---|---|---|
| | 441 | | | 450 | | | 459 | | | 468 | | | 477 | | | 486 | |
| A | P | V | F | P | L | G | Y | Q | Y | P | S | L | D | Q | L | A | D |

| ATG | ATC | CCT | TGC | GTC | CTG | CAG | TAC | CTA | AAT | TTC | TCT | ACA | ATA | ATT | GGA | GTT | GGT |
|---|---|---|---|---|---|---|---|---|---|---|---|---|---|---|---|---|---|
| | 495 | | | 504 | | | 513 | | | 522 | | | 531 | | | 540 | |
| M | I | P | C | V | L | Q | Y | L | N | F | S | T | I | I | G | V | G |

| GTT | GGA | GCT | GGA | GCC | TAC | ATC | CTG | GCG | AGA | TAT | GCT | CTT | AAC | CAC | CCG | GAC | ACT |
|---|---|---|---|---|---|---|---|---|---|---|---|---|---|---|---|---|---|
| | 549 | | | 558 | | | 567 | | | 576 | | | 585 | | | 594 | |
| V | G | A | G | A | Y | I | L | A | R | Y | A | L | N | H | P | D | T |

FIGURE 1B

```
      603           612           621           630           639           648
GTT GAA GGT CTT GTC CTC ATC AAC ATT GAT CCC AAT GCC AAG GGT TGG ATG GAT
 V   E   G   L   V   L   I   N   I   D   P   N   A   K   G   W   M   D 657           666           675           684           693           702
TGG GCA GCC CAC AAG CTA ACA GGC CTC ACC TCT ATT TCC ATT CCG GAG ATG ATC CTT
 W   A   A   H   K   L   T   G   L   T   S   I   S   I   P   E   M   I   L 711           720           729           738           747           756
GGA CAT CTT TTC AGC TTC AGC CTC TCT GGA AAT TCT GAG TTG ATA CAA AAG
 G   H   L   F   S   F   S   L   S   G   N   S   E   L   I   Q   K 765           774           783           792           801           810
TAC AGA AAT ATC ATT ACA CAT GCA CCC AAC CTG GAT AAC ATT GAA TTG TAC TGG
 Y   R   N   I   I   T   H   A   P   N   L   D   N   I   E   L   Y   W 819           828           837           846           855           864
AAC AGC TAC AAC AAC CGC CGA GAC CTG AAC TTT GAG CGT GGA GAT ATC ACC
 N   S   Y   N   N   R   R   D   L   N   F   E   R   G   D   I   T
```

FIGURE 1C

```
      873             882             891             900             909             918
CTC AGG TGT CCT GTG ATG CTG GTG GTA GGA GAC CAA GCA CCT CAT GAA GAT GCA
 L   R   C   P   V   M   L   V   V   G   D   Q   A   P   H   E   D   A 927             936             945             954             963             972
GTG GTG GAA TGT AAC TCA AAA CTG GAC CCC ACC CAG ACC TCG TTC CTC AAG ATG
 V   V   E   C   N   S   K   L   D   P   T   Q   T   S   F   L   K   M 981             990             999            1008            1017            1026
GCT GAC TCC GGA GGT CAG CCC CAG ACT CAG CCA GGC AAG CTG ACC GAG GCC
 A   D   S   G   G   Q   P   Q   T   Q   P   G   K   L   T   E   A 1035            1044            1053            1062            1071            1080
TTC AAG TAC TTC CTG CAA GGC ATG GGC TAC ATG GCC TCA TCC TGC ATG ACT CGC
 F   K   Y   F   L   Q   G   M   G   Y   M   A   S   S   C   M   T   R 1089            1098            1107            1116            1125            1134
CTG TCC CGG TCT CGT ACA GCC TCT CTG ACC AGT GCA GCA TCC GTT GAT GGC AAC
 L   S   R   S   R   T   A   S   L   T   S   A   A   S   V   D   G   N
```

FIGURE 1D

```
        1143            1152            1161            1170            1179            1188
CGG TCC CGC TCT CGC ACC CTG TCC CAG AGC AGC GAG TCT GGA ACT CTT TCT TCG
 R   S   R   S   R   T   L   S   Q   S   S   E   S   G   T   L   S   S 1197            1206            1215            1224            1233            1242
GGG CCC CCG GGG CAC ACC ATG GAG GTC TCC TGT TGA ATG GCC CTT GTT GCC CTA
 G   P   P   G   H   T   M   E   V   S   C 1251            1260            1269            1278            1287            1296
GAG TGG GAC CCA GCC CTC ACC TCC CCC AGA GCT AAC CTG GGA GGT GCT GAA GGG 1305            1314            1323            1332            1341            1350
GCA TTG GGC CAC CGT AAG CAA GGG AAA AAG GGC AGA TCA TGC GGG GAG ATG ACC 1359            1368            1377            1386            1395            1404
TTG ATC TTT GAT TGC TAC CCT AAC CTT GAC CTT TAA CCC GTG ATT CCC CCC AGC 1413            1422            1431            1440            1449            1458
TCC TGG AAG AGA TGT CCT AAT ATC TCT TAG GGA CCC AGA CCC CTA AAT TCT CCT 1467            1476            1485            1494            1503            1512
CCT CCC CCA TTT TGA TGT TAA GGT GGA GAG GGC ATA TGC ATC CTC TGT CCT GAT
```

FIGURE 1E

```
        1521           1530           1539           1548           1557           1566
CTA GGT GTC TAT AGC TGA GGG GTA AGA GGT TGT TGT AGT TGT CCT GGT GCC TCC
        1575           1584           1593           1602           1611           1620
ATC AGA CTC TCC CTA CTT GTC CCA TAT TTG CAA GGG GAG GGG ATT TGG GGC TGG
        1629           1638           1647           1656           1665           1674
GGC TCC ATT CAC CAA AGC TGA GGT GGC TTC TCA TTA ACC CTT TAG GAC TCT GAA
        1683           1692           1701           1710           1719           1728
GGG TAT GGA CCT ACG TGA ATG TGT GTC AGG GGG AGA CTT GCT GGT GGG TTA GTG
        1737           1746           1755           1764           1773           1782
GTC CTC AGG ATG TGA TAG AAA CAT CCA GTG TAA AAA GGA AGT TGG AAT GGG AGT
        1791           1800           1809           1818           1827           1836
TGG CGG GCA GTG AAC GAG TGT GGG GAA GGA TTG GTG CTG GGG CAA CAG GAA GGG
        1845           1854           1863           1872           1881           1890
GCC TGG GGC CGT TTG GCT GCA CTA ACT TTG GTA GCT CAG TGT GCA TCT AGA GTG
        1899           1908           1917           1926           1935           1944
GGA CTG GGG AGG GAG AGC TTG GGC TGG GCT GCT TGG GGC TTG GCA TAG GGT
```

FIGURE 1F

```
      1953      1962      1971      1980      1989      1998
GGA AAG GGC TAC CCT GGG GCT CTG ACC ACA CTG TAG TAT GTG TGG AGG GTG CCC
      2007      2016      2025      2034      2043      2052
TCC CGT CTC CCA CAA CTT CTG CTA TAA CAA TAA ACT GTA GAG GAA TCT GAA AAA

AAA 3'
```

FIGURE 1G

```
                 9           18           27      36           45        54
5' AGG CGC CGT AGG CTG GAA GCG CCA GCG CTG CCG GCG GGC GGT GTG ATT GAT CCG
   R   R   R   R   L   E   A   P   A   L   P   A   G   G   V   I   D   P 63           72           81      90           99        108
   CGT CCC CTG GAG CTG GAG GCT CGG GGG AAA GGG CCA GCA CGG AGC GGG CGC TCG
   R   P   L   E   L   E   A   R   G   K   G   P   A   R   S   G   R   S 117          126          135     144          153        162
   GTT GCT GCG CAC AAA GGC TGA GGC TCC AAG AGC TGC AGG GCG TGT TTG GGA CCC
   V   A   A   H   K   G   *   G   S   K   S   C   R   A   C   L   G   P 171          180          189     198          207        216
   CAG AGT CAG AAG GAG TGA GAA CCC TGA CCC CTA ATC CCA CTG CAT CCA GCC AAT
   Q   S   Q   K   E   *   E   P   *   P   L   I   P   L   H   P   A   N 225          234          243     252          261        270
   AGG AGC CCA GCC ACC ATG GCG GAG CTG CAG GAG GTG CAG ATC ACA GAG GAG AAG
   R   S   P   A   T   M   A   E   L   Q   E   V   Q   I   T   E   E   K

FIGURE 2A
```

```
    279         288         297         306         315         324
CCA CTG TTG CCA GGA CAG ACG CCT GAG GCG GCC AAG ACT CAC TCT GTG GAG ACA
 P   L   L   P   G   Q   T   P   E   A   A   K   T   H   S   V   E   T 333         342         351         360         369         378
CCA TAC GGC TCT GTC ACT TTC ACT GTC TAT GGC ACC CCC AAA CGC CCA
 P   Y   G   S   V   T   F   T   V   Y   G   T   P   K   R   P 387         396         405         414         423         432
GCG ATC CTT ACC TAC CAC GAT GTG GGA CTC AAC TAT AAA TCT TGC TTC CAG CCA
 A   I   L   T   Y   H   D   V   G   L   N   Y   K   S   C   F   Q   P 441         450         459         468         477         486
CTG TTT CAG TTC GAG GAC ATG CAG AAA ATC ATT CAG AAC TTT GTG CGG GTT CAT
 L   F   Q   F   E   D   M   Q   K   I   I   Q   N   F   V   R   V   H 495         504         513         522         531         540
GTG GAT GCC CCT GGA ATG GAA GAG GGA GCC CCT GTG TTC CCT TTG GGA TAT CAG
 V   D   A   P   G   M   E   E   G   A   P   V   F   P   L   G   Y   Q
```

FIGURE 2B

```
      549         558         567         576         585         594
TAC CCA TCT CTG GAC CAG CTT GCA GAC ATG ATC CCT TGC GTC CTG CAG TAC CTA
 Y   P   S   L   D   Q   L   A   D   M   I   P   C   V   L   Q   Y   L
      603         612         621         630         639         648
AAT TTC TCT ACA ATA ATT GGA GTT GGT GGA GCT GGA GCC TAC ATC CTG GCG
 N   F   S   T   I   I   G   V   G   G   A   G   A   Y   I   L   A
      657         666         675         684         693         702
AGA TAT GCT CTT AAC CAC CCG GAC ACT GTT GAA GGT CTT GTC CTC ATC AAC ATT
 R   Y   A   L   N   H   P   D   T   V   E   G   L   V   L   I   N   I
      711         720         729         738         747         756
GAT CCC AAT GCC AAG GGT TGG ATG GAT TGG GCA GCC CAC AAG CTA ACA GGC CTC
 D   P   N   A   K   G   W   M   D   W   A   A   H   K   L   T   G   L
      765         774         783         792         801         810
ACC TCT TCC ATT CCG GAG ATG ATC CTT GGA CAT CTT TTC AGC CAG GAA GAG CTC
 T   S   S   I   P   E   M   I   L   G   H   L   F   S   Q   E   E   L
```

FIGURE 2C

```
        819           828           837           846           855           864
TCT GGA AAT TCT GAG TTG ATA CAA AAG TAC AGA AAT ATC ATT ACA CAT GCA CCC
 S   G   N   S   E   L   I   Q   K   Y   R   N   I   I   T   H   A   P
        873           882           891           900           909           918
AAC CTG GAT AAC ATT GAA TTG TAC TGG AAC AGC TAC AAC AAC CGC CGA GAC CTG
 N   L   D   N   I   E   L   Y   W   N   S   Y   N   N   R   R   D   L
        927           936           945           954           963           972
AAC TTT GAG CGT GGA GGT GAT ATC ACC CTC AGG TGT CCT GTG ATG CTG GTG GTA
 N   F   E   R   G   G   D   I   T   L   R   C   P   V   M   L   V   V
        981           990           999          1008          1017          1026
GGA GAC CAA GCA CCT CAT GAA GAT GCA GTG GTG GAA TGT AAC TCA AAA CTG GAC
 G   D   Q   A   P   H   E   D   A   V   V   E   C   N   S   K   L   D
       1035          1044          1053          1062          1071          1080
CCC ACC CAG ACC TCG TTC CTC AAG ATG GCT GAC TCC GGA GGT CAG CCC CAG CTG
 P   T   Q   T   S   F   L   K   M   A   D   S   G   G   Q   P   Q   L
```

FIGURE 2D

```
         1089          1098          1107          1116          1125          1134
ACT CAG CCA GGC AAG CTG ACC GAG GCC TTC AAG TAC TTC CTG CAA GGC ATG GGC
 T   Q   P   G   K   L   T   E   A   F   K   Y   F   L   Q   G   M   G 1143          1152          1161          1170          1179          1188
TAC ATG GCC TCA TCC TGC ATG ACT CGC CTG TCC CGG TCT ACA GCC TCT CTG
 Y   M   A   S   S   C   M   T   R   L   S   R   S   T   A   S   L 1197          1206          1215          1224          1233          1242
ACC AGT GCA GCA TCC GTT GAT GGC NAC CGG TCC CGC TCT CGC ACC CTG TCC CAG
 T   S   A   A   S   V   D   G   X   R   S   R   S   R   T   L   S   Q 1251          1260          1269          1278          1287          1296
AGC AGC GAG TCT GGA ACT CTT TTC TTC GGG GGC CCC CGG CAC ACC ATG GGA
 S   S   E   S   G   T   L   F   F   G   G   P   R   H   T   M   G 1305          1314          1323          1332          1341          1350
GGT CTC CTG TTG AAT GGC CCT TGT TGC CCT AGA GTG GGA CCC AGC CCT CAG CTC
 G   L   L   L   N   G   P   C   C   P   R   V   G   P   S   P   Q   L
```

FIGURE 2E

```
        1359            1368            1377            1386            1395            1404
CCN CAG AGT AAC CTG NGA GGT GCT GAA AGG GGG CAT TGG GGC CAC CGT AAG CAA
 P   Q   S   N   L   X   G   A   E   R   G   H   W   G   H   R   K   Q 1413            1422            1431            1440            1449            1458
AGG GGA AAA AGG GCA GAT TCA TGG CGG GGG AGA TGA CCT TGA TTC TTT GAA TTG
 R   G   K   R   A   D   S   W   R   G   R   *   P   *   F   F   E   L 1467            1476            1485            1494            1503            1512
NNA ANC CTA ANC TTG AAC TTT AAN CCG TGA TTC CCC CCC AGC TCC TGG GAA GAN
 X   X   L   X   L   N   F   X   P   *   F   P   P   S   S   W   E   X 1521            1530            1539            1548            1557            1566
GAG GTC CTA ATN ATC TCT TAA GGG ACC CCA GAA CCC CTA AAA TTN CTC CGT CTT
 E   V   L   X   I   S   *   G   T   P   E   P   L   K   X   L   R   L 1575            1584            1593            1602            1611            1620
NCC CCA TTT TGA AGG TNA AAG GGG AAA AGG GGN ATA TGG AAT CCT CTG TTC CNG
 X   P   F   *   R   X   K   G   K   R   X   I   W   N   P   L   F   X
```

FIGURE 2F

```
        1629          1638          1647          1656          1665          1674
GAT TTA AGG GGT CCA AAN GTT GAG GGG GNA AAA GGT TGT GGN AAT TGG TCC CTG
 D   L   R   G   P   X   V   E   G   X   K   G   C   G   N   W   S   L 1683          1692          1701          1710          1719
GTG GCT CCA TCA AGA ATT TCC NAA ATT GTC CCA NAT TTT GNA AGG GGG GGG T 3'
 V   A   P   S   R   I   S   X   I   V   P   X   F   X   R   G   G
```

FIGURE 2G

```
  1  MA-ELQEVQITEEKPLLPGQTPEAAKEAEL---    2227688
  1  MA-ELQEVQITEEKPLLPGQTPEAAK----EKGETI  3507515
  1  MSREMQDVDLAEVKPLV------EKGETI          g1596167
  1  MA-ELQEVQITEEKPLLPGQTPETAKEAEL        g6141566

30  AARILLDQGQTHSVETPYGSVTFTVYGTPK         2227688
 26  ---THSVETPYGSVTFTVYGTPK                3507515
 24  TGLLQEFDVQEQDIETLHGSVHVTLCGTPK         g1596167
 30  AARILLDQGQTHSVETPYGSVTFTVYGTPK         g6141566

60  PKRPAILTYHDVGLNYKSCFQPLFQFEDMQ         2227688
 46  PKRPAILTYHDVGLNYKSCFQPLFQFEDMQ         3507515
 54  GNRPVILTYHDIGMNHKTCYNPLFNYEDMQ         g1596167
 60  PKRPAIFTYHDVGLNYKSCFQPLFRFGDMQ         g6141566

90  EIIQNFVRVHVDAPGMEEGAPVFPLGYQYP         2227688
 76  EIIQNFVRVHVDAPGMEEGAPVFPLGYQYP         3507515
 84  EITQHFAVCHVDAPGQQDGAASFPAGYMYP         g1596167
 90  EIIQNFVRVHVDAPGMEEGAPVFPLGYQYP         g6141566

120  SLDQLADMIPCVLQYLNFSTIIGVGVGAGA         2227688
106  SLDQLADMIPCVLQYLNFSTIIGVGVGAGA         3507515
114  SMDQLAEMLPGVLQQFGLKSIIGMGTGAGA         g1596167
120  SLDQLADMIPCILQYLNFSTIIGVGVGAGA         g6141566
```

| | | | |
|---|---|---|---|
| 296 | QLTQPGKLTEAFKYFLQGMGYMASSCMTRL | 2227688 |
| 282 | QLTQPGKLTEAFKYFLQGMGYMASSCMTRL | 3507515 |
| 294 | QISQPAKLAEAFKYFVQGMGYMPSASMTRL | g1596167 |
| 296 | QLTQPGKLTEAFKYFLQGMGYMASSCMTRL | g6141566 |
| | | | |
| 326 | SRSRSRTASLTSAAASVDGNRSRSRTLSQSSES | 2227688 |
| 312 | SRSRSRTASLTSAAASVDGXRSRSRTLSQSSES | 3507515 |
| 324 | MRSRTASGSVTSLDGTRSRSHT-SEGTRS | g1596167 |
| 326 | SRSRSRTASLTSAASIDGSRSRSRTLSQSSES | g6141566 |
| | | | |
| 356 | GTLS-SGPPGHTM--------------- | 2227688 |
| 342 | GTLFFGGPRGHTMGGLLLNGPCCPRVGPSP | 3507515 |
| 353 | RSHTSEGTRSRS------HTSEGA--- | g1596167 |
| 356 | GTLP-SGPPGHTM--------------- | g6141566 |
| | | | |
| 368 | EVS--C-------QLXGAERGHWGHRKQRGKRADSWRG | 2227688 |
| 372 | QLXQSNLXGAERGHWGHRKQRGKRADSWRG | 3507515 |
| 371 | HLDITPNSGAA-GNSAGPKSMEVSC | g1596167 |
| 368 | EVS--C------------------ | g6141566 |
| | | | |
| 371 | | 2227688 |
| 402 | R | 3507515 |
| 394 | | g1596167 |
| 371 | | g6141566 |

FIGURE 3C

SEQUENCE LISTING

<160> NUMBER OF SEQ ID NOS: 33

<210> SEQ ID NO 1
<211> LENGTH: 371
<212> TYPE: PRT
<213> ORGANISM: Homo sapiens
<220> FEATURE:
<221> NAME/KEY: misc_feature
<223> OTHER INFORMATION: Incyte ID No: 2227688CD1

<400> SEQUENCE: 1

```
Met Ala Glu Leu Gln Glu Val Gln Ile Thr Glu Glu Lys Pro Leu
 1               5                  10                  15

Leu Pro Gly Gln Thr Pro Glu Ala Ala Lys Glu Ala Glu Leu Ala
                20                  25                  30

Ala Arg Ile Leu Leu Asp Gln Gly Gln Thr His Ser Val Glu Thr
                35                  40                  45

Pro Tyr Gly Ser Val Thr Phe Thr Val Tyr Gly Thr Pro Lys Pro
                50                  55                  60

Lys Arg Pro Ala Ile Leu Thr Tyr His Asp Val Gly Leu Asn Tyr
                65                  70                  75

Lys Ser Cys Phe Gln Pro Leu Phe Gln Phe Glu Asp Met Gln Glu
                80                  85                  90

Ile Ile Gln Asn Phe Val Arg Val His Val Asp Ala Pro Gly Met
                95                 100                 105

Glu Glu Gly Ala Pro Val Phe Pro Leu Gly Tyr Gln Tyr Pro Ser
               110                 115                 120

Leu Asp Gln Leu Ala Asp Met Ile Pro Cys Val Leu Gln Tyr Leu
               125                 130                 135

Asn Phe Ser Thr Ile Ile Gly Val Gly Val Gly Ala Gly Ala Tyr
               140                 145                 150

Ile Leu Ala Arg Tyr Ala Leu Asn His Pro Asp Thr Val Glu Gly
               155                 160                 165

Leu Val Leu Ile Asn Ile Asp Pro Asn Ala Lys Gly Trp Met Asp
               170                 175                 180

Trp Ala Ala His Lys Leu Thr Gly Leu Thr Ser Ser Ile Pro Glu
               185                 190                 195

Met Ile Leu Gly His Leu Phe Ser Gln Glu Glu Leu Ser Gly Asn
               200                 205                 210

Ser Glu Leu Ile Gln Lys Tyr Arg Asn Ile Ile Thr His Ala Pro
               215                 220                 225

Asn Leu Asp Asn Ile Glu Leu Tyr Trp Asn Ser Tyr Asn Asn Arg
               230                 235                 240

Arg Asp Leu Asn Phe Glu Arg Gly Gly Asp Ile Thr Leu Arg Cys
               245                 250                 255

Pro Val Met Leu Val Val Gly Asp Gln Ala Pro His Glu Asp Ala
```

-continued

```
                    260                 265                 270
Val Val Glu Cys Asn Ser Lys Leu Asp Pro Thr Gln Thr Ser Phe
                275                 280                 285
Leu Lys Met Ala Asp Ser Gly Gly Gln Pro Gln Leu Thr Gln Pro
                290                 295                 300
Gly Lys Leu Thr Glu Ala Phe Lys Tyr Phe Leu Gln Gly Met Gly
                305                 310                 315
Tyr Met Ala Ser Ser Cys Met Thr Arg Leu Ser Arg Ser Arg Thr
                320                 325                 330
Ala Ser Leu Thr Ser Ala Ala Ser Val Asp Gly Asn Arg Ser Arg
                335                 340                 345
Ser Arg Thr Leu Ser Gln Ser Ser Glu Ser Gly Thr Leu Ser Ser
                350                 355                 360
Gly Pro Pro Gly His Thr Met Glu Val Ser Cys
                365                 370

<210> SEQ ID NO 2
<211> LENGTH: 402
<212> TYPE: PRT
<213> ORGANISM: Homo sapiens
<220> FEATURE:
<221> NAME/KEY: misc_feature
<223> OTHER INFORMATION: Incyte ID No: 3507515CD1
<221> NAME/KEY: unsure
<222> LOCATION: 328, 374, 379
<223> OTHER INFORMATION: unknown or other

<400> SEQUENCE: 2

Met Ala Glu Leu Gln Glu Val Gln Ile Thr Glu Glu Lys Pro Leu
  1               5                  10                  15
Leu Pro Gly Gln Thr Pro Glu Ala Ala Lys Thr His Ser Val Glu
                 20                  25                  30
Thr Pro Tyr Gly Ser Val Thr Phe Thr Val Tyr Gly Thr Pro Lys
                 35                  40                  45
Pro Lys Arg Pro Ala Ile Leu Thr Tyr His Asp Val Gly Leu Asn
                 50                  55                  60
Tyr Lys Ser Cys Phe Gln Pro Leu Phe Gln Phe Glu Asp Met Gln
                 65                  70                  75
Glu Ile Ile Gln Asn Phe Val Arg Val His Val Asp Ala Pro Gly
                 80                  85                  90
Met Glu Glu Gly Ala Pro Val Phe Pro Leu Gly Tyr Gln Tyr Pro
                 95                 100                 105
Ser Leu Asp Gln Leu Ala Asp Met Ile Pro Cys Val Leu Gln Tyr
                110                 115                 120
Leu Asn Phe Ser Thr Ile Ile Gly Val Gly Val Gly Ala Gly Ala
                125                 130                 135
Tyr Ile Leu Ala Arg Tyr Ala Leu Asn His Pro Asp Thr Val Glu
                140                 145                 150
Gly Leu Val Leu Ile Asn Ile Asp Pro Asn Ala Lys Gly Trp Met
                155                 160                 165
Asp Trp Ala Ala His Lys Leu Thr Gly Leu Thr Ser Ser Ile Pro
                170                 175                 180
Glu Met Ile Leu Gly His Leu Phe Ser Gln Glu Glu Leu Ser Gly
                185                 190                 195
Asn Ser Glu Leu Ile Gln Lys Tyr Arg Asn Ile Ile Thr His Ala
                200                 205                 210
```

```
Pro Asn Leu Asp Asn Ile Glu Leu Tyr Trp Asn Ser Tyr Asn Asn
                215                 220                 225

Arg Arg Asp Leu Asn Phe Glu Arg Gly Gly Asp Ile Thr Leu Arg
            230                 235                 240

Cys Pro Val Met Leu Val Gly Asp Gln Ala Pro His Glu Asp
            245                 250                 255

Ala Val Val Glu Cys Asn Ser Lys Leu Asp Pro Thr Gln Thr Ser
        260                 265                 270

Phe Leu Lys Met Ala Asp Ser Gly Gly Gln Pro Gln Leu Thr Gln
            275                 280                 285

Pro Gly Lys Leu Thr Glu Ala Phe Lys Tyr Phe Leu Gln Gly Met
            290                 295                 300

Gly Tyr Met Ala Ser Ser Cys Met Thr Arg Leu Ser Arg Ser Arg
            305                 310                 315

Thr Ala Ser Leu Thr Ser Ala Ala Ser Val Asp Gly Xaa Arg Ser
            320                 325                 330

Arg Ser Arg Thr Leu Ser Gln Ser Ser Glu Ser Gly Thr Leu Phe
            335                 340                 345

Phe Gly Gly Pro Arg Gly His Thr Met Gly Gly Leu Leu Leu Asn
            350                 355                 360

Gly Pro Cys Cys Pro Arg Val Gly Pro Ser Pro Gln Leu Xaa Gln
            365                 370                 375

Ser Asn Leu Xaa Gly Ala Glu Arg Gly His Trp Gly His Arg Lys
            380                 385                 390

Gln Arg Gly Lys Arg Ala Asp Ser Trp Arg Gly Arg
            395                 400

<210> SEQ ID NO 3
<211> LENGTH: 2055
<212> TYPE: DNA
<213> ORGANISM: Homo sapiens
<220> FEATURE:
<221> NAME/KEY: misc_feature
<223> OTHER INFORMATION: Incyte ID No: 2227688CB1

<400> SEQUENCE: 3
agagcaggcg tcgggacgca gcaaagagag gagagacccc agagtcagaa ggagtgagaa      60
ccctgacccc taatcccact gcatccagcc aataggagcc cagccaccat ggcggagctg     120
caggaggtgc agatcacaga ggagaagcca ctgttgccag acagacgcc tgaggcggcc      180 aaggaggctg agttagctgc ccgaatcctc ctggaccagg acagactca ctctgtggag      240 acaccatacg gctctgtcac tttcactgtc tatggcaccc ccaaacccaa cgcccagcg     300 atccttacct accacgatgt gggactcaac tataaatctt gcttccagcc actgtttcag     360
ttcgaggaca tgcaggaaat cattcagaac tttgtgcggg ttcatgtgga tgcccctgga     420
atggaagagg gagcccctgt gttccctttg ggatatcagt acccatctct ggaccagctt     480
gcagacatga tcccttgcgt cctgcagtac ctaaatttct ctacaataat tggagttggt     540
gttggagctg gagcctacat cctggcgaga tatgctctta accacccgga cactgttgaa     600
ggtcttgtcc tcatcaacat tgatcccaat gccaagggtt ggatggattg gcagcccac     660 aagctaacag gcctcaccct cttccattcc gagatgatcc ttggacatct tttcagccag     720
gaagagctct ctggaaattc tgagttgata caaaagtaca gaaatatcat tacacatgca     780
cccaacctgg ataacattga attgtactgg aacagctaca caaccgccg agacctgaac     840 tttgagcgtg gaggtgatat caccctcagg tgtcctgtga tgctggtggt aggagaccaa     900
```

```
gcacctcatg aagatgcagt ggtggaatgt aactcaaaac tggaccccac ccagacctcg      960
ttcctcaaga tggctgactc cggaggtcag ccccagctga ctcagccagg caagctgacc     1020
gaggccttca agtacttcct gcaaggcatg ggctacatgg cctcatcctg catgactcgc     1080
ctgtcccggt ctcgtacagc ctctctgacc agtgcagcat ccgttgatgg caaccggtcc     1140
cgctctcgca ccctgtccca gagcagcgag tctggaactc tttcttcggg gccccgggg      1200 cacaccatgg aggtctcctg ttgaatggcc cttgttgccc tagagtggga cccagccctc     1260
acctccccca gagctaacct gggaggtgct gaaggggcat tgggccaccg taagcaaggg     1320
aaaaagggca gatcatgcgg ggagatgacc ttgatctttg attgctaccc taaccttgac     1380
ctttaacccg tgattccccc cagctcctgg aagagatgtc ctaatatctc ttagggaccc     1440
agacccctaa attctcctcc tcccccattt tgatgttaag gtggagaggg catatgcatc     1500
ctctgtcctg atctaggtgt ctatagctga ggggtaagag gttgttgtag ttgtcctggt     1560
gcctccatca gactctccct acttgtccca tatttgcaag gggaggggat ttggggctgg     1620
ggctccattc accaaagctg aggtggcttc tcattaaccc tttaggactc tgaagggtat     1680
ggacctacgt gaatgtgtgt caggggagac ttgctggtg ggttagtggt cctcaggatg      1740
tgatagaaac atccagtgta aaaggaagt tggaatggga gttggcgggc agtgaacgag       1800
tgtggggaag gattggtgct ggggcaacag gaagggggcct ggggccgttt ggctgcacta    1860
actttggtag ctcagtgtgc atctagagtg ggactgggga gggagctaag cttgggctgg     1920
gctgcttggg gcttggcata gggtggaaag ggctaccctg gggctctgac cacactgtag     1980
tatgtgtgga gggtgccctc ccgtctccca caacttctgc tataacaata aactgtagag     2040
gaatctgaaa aaaaa                                                      2055

<210> SEQ ID NO 4
<211> LENGTH: 228
<212> TYPE: DNA
<213> ORGANISM: Homo sapiens
<220> FEATURE:
<221> NAME/KEY: misc_feature
<223> OTHER INFORMATION: Incyte ID No: 2227688H1
<221> NAME/KEY: unsure
<222> LOCATION: 60
<223> OTHER INFORMATION: a, t, c, g, or other

<400> SEQUENCE: 4 ggggttggatg gattgggcag cccacaagct aacaggcctc acctcttcca ttccggagan      60
gatccttgga catcttttca gccaggaaga gctctctgga aattctgagt tgatacaaaa     120
gtacagaaat atcattacac atgcacccaa cctggataac attgaattgt actggaacag     180
ctacaacaac cgccgagacc tgaactttga gcgtggaggt gatatcac                  228

<210> SEQ ID NO 5
<211> LENGTH: 285
<212> TYPE: DNA
<213> ORGANISM: Homo sapiens
<220> FEATURE:
<221> NAME/KEY: misc_feature
<223> OTHER INFORMATION: Incyte ID No: 3507515H1
<221> NAME/KEY: unsure
<222> LOCATION: 22, 35-36, 38, 51
<223> OTHER INFORMATION: a, t, c, g, or other

<400> SEQUENCE: 5 ggcgagggc cgtaggcctg gnaaggcgcc agcgnngncc ggcgggcggt ngtgattgat        60
```

| | |
|---|---|
| ccgcgtcccc tggagctgga ggctcggggg aaagggccag aacggagcgg gcgctcggtt | 120 |
| gctgcgcaca aaggctgagg ctccaagagc tgcaggcgt gtttgggacc ccagagtcag | 180 |
| aaggagtgag aaccctgacc cctaatccca ctgcatccag ccaataggag cccagccacc | 240 |
| atggcggagc tgcaggaggt gcagatcaca gaggagaagc cactg | 285 |

<210> SEQ ID NO 6
<211> LENGTH: 844
<212> TYPE: DNA
<213> ORGANISM: Homo sapiens
<220> FEATURE:
<221> NAME/KEY: misc_feature
<223> OTHER INFORMATION: Incyte ID No: 027805X7
<221> NAME/KEY: unsure
<222> LOCATION: 116, 297-298, 551, 554, 628, 706, 711, 755, 767, 780,
     798, 800
<223> OTHER INFORMATION: a, t, c, g, or other

<400> SEQUENCE: 6

| | |
|---|---|
| cgcccccct ccccgccttg ttgtcctact tctcccggag cagccggaga gcaggcgtcg | 60 |
| ggacgcagca aagagaggag aggccaccat ggcggagctg caggaggtgc agatcncaga | 120 |
| ggagaagcca ctgttgccag acagacgcc tgaggcggcc aagactcact ctgtggagac | 180 |
| accatacggc tctgtcactt tcactgtcta tggcacccc aaacccaaac gcccagcgat | 240 |
| ccttacctac cacgatgtgg gactcaacta taaatcttgc ttccagccac tgtttcnntt | 300 |
| cgaggacatg caggaaatca ttcagaactt tgtgcgggtt catgtggatg cccctggaat | 360 |
| ggaagaggga gcccctgtgt tccctttggg atatcagtac ccatctctgg accagcttgc | 420 |
| agacatgatc ccttgcgtcc tgcagtacct aaatttctct acaataattg agttggtgt | 480 |
| tggagctgga gcctacatcc tggcgagata tgctcttaac cacccggaca ctgttgaagg | 540 |
| tcttgtcctc ntcnacattg atcccaatgc caagggttgg atggattggg cagcccacaa | 600 |
| gctaacaggc ctcacctctt ccattccnga gatgatcctt ggacatcttt tcagccagga | 660 |
| aaaactctct ggaaattctg aattgataca aaatacagaa atatcnttac ncatgcacca | 720 |
| acctggataa cattgaattg tactggaaca ctacnacaac cgccaanact gaactttgan | 780 |
| cgtggaagta tatcaccncn ggtttctgtg atctggtggt aggaaacaac ccctcttgaa | 840 |
| gagc | 844 |

<210> SEQ ID NO 7
<211> LENGTH: 528
<212> TYPE: DNA
<213> ORGANISM: Homo sapiens
<220> FEATURE:
<221> NAME/KEY: misc_feature
<223> OTHER INFORMATION: Incyte ID No: 1300824F1
<221> NAME/KEY: unsure
<222> LOCATION: 20, 396, 446, 478
<223> OTHER INFORMATION: a, t, c, g, or other

<400> SEQUENCE: 7

| | |
|---|---|
| gctgccccg acactgttn taaggtcttg tcctcatcaa cattgatccc aatgccaagg | 60 |
| gttggatgga ttgggcagcc cacaagctaa caggcctcac ctcttccatt ccggagatga | 120 |
| tccttggaca tctttttcagc caggaagagc tctctgaaa ttctgagttg atacaaaagt | 180 |
| acagaaatat cattacacat gcacccaacc tggataacat tgaattgtac tggaacagct | 240 |
| acaacaaccg ccgagacctg aactttgagc gtggaggtga tatcaccctc aggtgtcctg | 300 |
| tgatgctggt ggtaggagac caagcacctc atgaagatgc agtggtggaa tgtaactcaa | 360 |

-continued

| aaactggacc ccacccagac ctcgttcctc aagatngctg actccggagg tcagcccag | 420 |
| ctgactcagc caggaagctg accganggct tcaagtactt ctgcaaggca tgggctanat | 480 |
| tggctcatcc tgcatgactc gctgtccggg tctcgtaaaa gctctctt | 528 |

<210> SEQ ID NO 8
<211> LENGTH: 593
<212> TYPE: DNA
<213> ORGANISM: Homo sapiens
<220> FEATURE:
<221> NAME/KEY: misc_feature
<223> OTHER INFORMATION: Incyte ID No: 1384447F1
<221> NAME/KEY: unsure
<222> LOCATION: 347, 538, 573
<223> OTHER INFORMATION: a, t, c, g, or other

<400> SEQUENCE: 8

| gcaaggcatg ggctacatgg cctcatcctg catgactcgc ctgtcccggt ctcgtacagc | 60 |
| ctctctgacc agtgcagcat ccgttgatgg caaccggtcc cgctctcgca ccctgtccca | 120 |
| gagcagcgag tctggaactc tttcttcggg gccccccggg cacaccatgg aggtctcctg | 180 |
| ttgaatggcc cttgttgccc tagagtggga cccagccctc acctccccca gagctaacct | 240 |
| gggaggtgct gaaggggcat tgggccaccg taagcaaggg aaaaagggca gatcatgcgg | 300 |
| ggagatgacc ttgatctttg attgctaccc taaccttgac ctttaaccg tgattccccc | 360 |
| cagtcctgga agagatgtcc taatatctct tagggaccag acccctaaat tctcctcctc | 420 |
| ccccattttg atgttaaggt ggagaaggca tatgatctct gtcctgatct agtgtctaat | 480 |
| aagcttaagg ggtaagaggt tgttgtagtt gtcctggtgc tccatcagat tctcccantt | 540 |
| ggcccatatt gcaagggaa gggatttggg gtngggtcc atttaaccaa agt | 593 |

<210> SEQ ID NO 9
<211> LENGTH: 785
<212> TYPE: DNA
<213> ORGANISM: Homo sapiens
<220> FEATURE:
<221> NAME/KEY: misc_feature
<223> OTHER INFORMATION: Incyte ID No: 1291929T1
<221> NAME/KEY: unsure
<222> LOCATION: 18, 35, 200, 499, 522, 529, 531, 571, 596, 600, 607,
      619, 645, 672, 679, 691, 719, 727, 731-732, 736, 742, 748, 765
<223> OTHER INFORMATION: a, t, c, g, or other

<400> SEQUENCE: 9

| tacagtttat tgttatanca gaagttgtgg gagangggag ggcacctcca cacatactac | 60 |
| agtgtggtca gagccccagg gtagcccttt ccaccctatg ccaagcccca agcagcccag | 120 |
| cccaagctta gctccctccc cagtcccact ctagatgcac actgagctac caaagttagt | 180 |
| gcagccaaac ggcccccaggn cccttcctgt tgccccagca ccaatccttc cccacactcg | 240 |
| ttcactgccc gccaactccc attccaactt ccttttttaca ctggatgttt ctatcacatc | 300 |
| ctgaggacca ctaacccacc agcaagtctc ccctgacac acattcacgt aggtccatac | 360 |
| ccttcagagt cctaaagggt taatgagaag cacctcagct ttggtgaatg gagcccagcc | 420 |
| caaatccctc cccttgcaaa tatggcaagt agggagagtt gatggaggac caggacaact | 480 |
| acaacaactt tttaccccna agtatagaca cctagattag gncagaggnt natatgcctc | 540 |
| ttcaacttaa cacccaaatg ggggaggagg ngaatttagg ggtctggggc ctaagnggtn | 600 |
| ttagggnatt ctcttccang agcttggggg ggatcaccgg ggttnaaagg tcaaagggtt | 660 |
| aagggtggca antcaaagnt tcaagggtat nttccccgg atggatttgg ccctttttnc | 720 |

```
ccttggntta nngggnggggc cnaattgncc cctttaggga acttncccag ggtttagtct    780
tggggg                                                                785

<210> SEQ ID NO 10
<211> LENGTH: 225
<212> TYPE: DNA
<213> ORGANISM: Homo sapiens
<220> FEATURE:
<221> NAME/KEY: misc_feature
<223> OTHER INFORMATION: Incyte ID No: 1367779H1

<400> SEQUENCE: 10 gaagggggcct ggggccgttt ggctgcacta actttggtag ctcagtgtgc atctagagtg    60
ggactgggga gggagctaag cttgggctgg gctgcttggg gcttggcata gggtggaaag    120 ggctacccctg gggctctgac cacactgtag tatgtgtgga gggtgccctc ccgtctccca    180
caacttctgc tataacaata aactgtagag gaatctgaaa aaaaa                   225

<210> SEQ ID NO 11
<211> LENGTH: 1726
<212> TYPE: DNA
<213> ORGANISM: Homo sapiens
<220> FEATURE:
<221> NAME/KEY: misc_feature
<223> OTHER INFORMATION: Incyte ID No: 3507515CT1
<221> NAME/KEY: unsure
<222> LOCATION: 1213, 1353, 1366, 1459-1460, 1463, 1469, 1482, 1512,
      1524, 1557, 1567, 1583, 1599, 1619, 1638, 1649, 1662, 1696, 1708,
      1715
<223> OTHER INFORMATION: a, t, c, g, or other

<400> SEQUENCE: 11
aggcgccgta ggctggaagc gccagcgctg ccggcgggcg gtgtgattga tccgcgtccc    60
ctggagctgg aggctcgggg gaaagggcca gcacggagcg ggcgctcggt tgctgcgcac    120
aaaggctgag gctccaagag ctgcagggcg tgtttgggac cccagagtca gaaggagtga    180
gaaccctgac ccctaatccc actgcatcca gccaatagga gcccagccac catggcggag    240
ctgcaggagg tgcagatcac agaggagaag ccactgttgc caggacagac gcctgaggcg    300
gccaagactc actctgtgga gacaccatac ggctctgtca cttttcactgt ctatggcacc    360 cccaaaccca aacgcccagc gatccttacc taccacgatg tgggactcaa ctataaatct    420
tgcttccagc cactgtttca gttcgaggac atgcaggaaa tcattcagaa cttttgtgcgg    480 gttcatgtgg atgcccctgg aatggaagag ggagcccctg tgttcccttt gggatatcag    540
tacccatctc tggaccagct tgcagacatg atcccttgcg tcctgcagta cctaaatttc    600
tctacaataa ttggagttgg tgttggagct ggagcctaca tcctggcgag atatgctctt    660
aaccacccgg acactgttga aggtcttgtc ctcatcaaca ttgatcccaa tgccaagggt    720
tggatggatt gggcagccca caagctaaca ggcctcacct cttccattcc ggagatgatc    780
cttggacatc ttttcagcca ggaagagctc tctggaaatt ctgagttgat acaaaagtac    840
agaaatatca ttcacacatgc acccaacctg gataacattg aattgtactg gaacagctac    900
aacaaccgcc gagacctgaa ctttgagcgt ggaggtgata tcaccctcag gtgtcctgtg    960
atgctggtgg taggagacca agcacctcat gaagatcag tggtgaatg taactcaaaa    1020 ctggacccca cccagaccct cgttcctcaag atggctgact ccggaggtca gccccagctg    1080
actcagccag gcaagctgac cgaggccttc aagtacttcc tgcaaggcat gggctacatg    1140
gcctcatcct gcatgactcg cctgtcccgg tctcgtacag cctctctgac cagtgcagca    1200
```

-continued

```
tccgttgatg gcnaccggtc ccgctctcgc accctgtccc agagcagcga gtctggaact    1260
cttttcttcg ggggcccccg gggcacacc atgggaggtc tcctgttgaa tggcccttgt    1320
tgccctagag tgggacccag ccctcagctc ccncagagta acctgngagg tgctgaaagg    1380
gggcattggg gccaccgtaa gcaaagggga aaaagggcag attcatggcg ggggagatga    1440
ccttgattct ttgaattgnn aancctaanc ttgaacttta anccgtgatt ccccccccagc    1500 tcctgggaag angaggtcct aatnatctct taagggaccc cagaacccct aaaattnctc    1560
cgtcttnccc cattttgaag gtnaaagggg aaaaggggna tatggaatcc tctgttccng    1620
gatttaaggg gtccaaangt tgagggggna aaaggttgtg gnaattggtc cctggtggct    1680
ccatcaagaa tttccnaaat tgtcccanat tttgnaaggg ggggt                    1726
```

<210> SEQ ID NO 12
<211> LENGTH: 584
<212> TYPE: DNA
<213> ORGANISM: Homo sapiens
<220> FEATURE:
<221> NAME/KEY: misc_feature
<223> OTHER INFORMATION: Incyte ID No: 3507515F6
<221> NAME/KEY: unsure
<222> LOCATION: 8, 34-35, 246
<223> OTHER INFORMATION: a, t, c, g, or other

<400> SEQUENCE: 12

```
ggcgaggngc cgtaggcctg gaaggcgcca gcgnngccgg cggcggtgt gattgatccg      60 cgtcccctgg agctggaggc tcgggggaaa gggccagcac ggagcgggcg ctcggttgct    120
gcgcacaaag gctgaggctc caagagctgc agggcgtgtt tgggacccca gagtcagaag    180
gagtgagaac cctgaccct aatcccactg catccagcca ataggagccc agccaccatg    240
gcggantgca ggaggtgcag atcacagagg agaagccact gttgccagga cagacgcctg    300
aggcggccaa gactcactct gtggagacac catacggctc tgtcactttc actgtctatg    360 gcaccccaa acccaaacgc ccagcgatcc ttacctacca cgatgtggga ctcaactata    420
aatcttgctt ccagccactg tttcagttcg aggacatgca ggaaatcatt cagaactttg    480
tgcgggttca tgtggatgcc cctggaatgg aagagggagc ccctgtgttc cctttgggat    540
atcagtaccc atctctggac cagcttgcag acatgatccc tttg                     584
```

<210> SEQ ID NO 13
<211> LENGTH: 578
<212> TYPE: DNA
<213> ORGANISM: Homo sapiens
<220> FEATURE:
<221> NAME/KEY: misc_feature
<223> OTHER INFORMATION: Incyte ID No: 1214191R1
<221> NAME/KEY: unsure
<222> LOCATION: 92-93, 341, 567
<223> OTHER INFORMATION: a, t, c, g, or other

<400> SEQUENCE: 13

```
gcttgcttcc agccactgtt tcagttcgag gacatgcagg aaatcattca gaactttgtg     60
cgggttcatg tggatgcccc tggaatggaa gnncggagcc cctgtgttcc ctttgggata    120
tcagtaccca tctctggacc agcttgcaga catgatccct tgcgtcctgc agtacctaaa    180
tttctctaca ataattggag ttggtgttgg agctggagcc tacatcctgg cgagatatgc    240
tcttaaccaa ccggacactg ttgaaggtct tgtcctcatc aacattgatt ccaatgccaa    300
gggttggatg gattgggcag cccacaagct aacaggctca nctcttccat tccggagatg    360
atccttggac atcttttcag ccaggaagag tctctggaaa ttctgagttg atacaaagta    420
```

```
cagaaatatc attacacatg caaccaacct ggataacatt gaattgtact ggaacagcta      480
caacaaccgg ccgagacctg aactttgagc gtggaggtga tatcaccctc aggtgtcctg      540
tgatgctggt ggtagcagac caagcanctc atgaagat                             578
```

<210> SEQ ID NO 14
<211> LENGTH: 569
<212> TYPE: DNA
<213> ORGANISM: Homo sapiens
<220> FEATURE:
<221> NAME/KEY: misc_feature
<223> OTHER INFORMATION: Incyte ID No: 3364735F6
<221> NAME/KEY: unsure
<222> LOCATION: 160, 484, 518, 538, 556, 562
<223> OTHER INFORMATION: a, t, c, g, or other

<400> SEQUENCE: 14

```
gttggagctg gagcctacat cctggcgaga tatgctctta accacccgga cactgttgaa      60
ggtcttgtcc tcatcaacat tgatcccaat gccaagggtt ggatggattg ggcagcccac     120
aagctaacag gcctcacctc ttccattccg gagatgatcn ttggacatct tttcagccag     180
gaagagctct ctggaaattc tgagttgata caaaagtaca gaaatatcat tacacatgca     240
cccaacctgg ataacattga attgtactgg aacagctaca caaccgccg agacctgaac      300 tttgagcgtg gaggtgatat caccctcagg tgtcctgtga tgctggtggt aggagaccaa     360
gcacctcatg aagatgcagt ggtggaatgt aactcaaaat tggaccccca cccagacctc     420
gttcctcaag atggctgact ccggaggtca gccccagctg actcagccag gcaagctgac     480
cganggcctt caagtacttt cctgcaggca tgggctanat ggcctcatct gatgactngc     540
ttgtccgggt tcgtanagcc tnttgacca                                        569
```

<210> SEQ ID NO 15
<211> LENGTH: 913
<212> TYPE: DNA
<213> ORGANISM: Homo sapiens
<220> FEATURE:
<221> NAME/KEY: misc_feature
<223> OTHER INFORMATION: Incyte ID No: 1289617F1
<221> NAME/KEY: unsure
<222> LOCATION: 400, 540, 553, 646-647, 650, 656, 669, 699, 711, 744,
       754, 770, 786, 806, 825, 836, 849, 883, 895, 902
<223> OTHER INFORMATION: a, t, c, g, or other

<400> SEQUENCE: 15

```
ggaaattctg agttgataca aaagtacaga aatatcatta cacatgcacc caacctggat      60
aacattgaat tgtactggaa cagctacaac aaccgccgag acctgaactt tgagcgtgga    120
ggtgatatca ccctcaggtg tcctgtgatg ctggtggtag agaccaagc acctcatgaa     180 gatgcagtgg tggaatgtaa ctcaaaactg acccccaccc agacctcgtt cctcaagatg    240
gctgactccg gaggtcagcc ccagctgact cagccaggca agctgaccga ggccttcaag    300
tacttcctgc aaggcatggg ctacatggcc tcatcctgca tgactcgcct gtcccggtct    360
cgtacagcct ctctgaccag tgcagcatcc gttgatggcn accggtcccg ctctcgcacc    420
ctgtcccaga gcagcgagtc tggaactctt ttcttcgggg gccccgggg cacaccatg      480 ggaggtctcc tgttgaatgg cccttgttgc cctagagtgg gacccagccc tcagctcccn    540
cagagtaacc tgngaggtgc tgaaaggggg cattggggcc accgtaagca aggggaaaa     600 agggcagatt catgcggggg agatgacct tgattctttg aattgnnaan cctaancttg      660
aactttaanc cgtgattccc ccccagctcc tgggaagang aggtcctaat natctcttaa    720
```

```
gggaccccag aaccccctaaa attnctccgt cttncccccat tttgaaggtn aaagggggaaa    780 agggnatat  ggaatcctct gttccnggat ttaagggtc  caaangttga gggggnaaaa       840
ggttgtggna attggtccct ggtggctcca tcaagaattt ccnaaattgt cccanatttt       900 gnaaggggg  ggt                                                          913
```

```
<210> SEQ ID NO 16
<211> LENGTH: 265
<212> TYPE: DNA
<213> ORGANISM: Macaca fascicularis
<220> FEATURE:
<221> NAME/KEY: misc_feature
<223> OTHER INFORMATION: Incyte ID No: 700718124H1

<400> SEQUENCE: 16
ccaaacccaa acgcccagcg atccttacct accacgatgt gggactcaac tataaatctt    60
gcttccagcc actgtttcaa ttcggggaca tgcaggaaat cattcagaac ttcgtgcggg   120
ttcatgtgga tgcccctgga atggaagagg gagcccctgt gttccctttg ggatatcagt   180
acccatctct ggaccagctt gcagacatga tcccttgcgt cctacagtac ctaaattttt   240
ctacagtaat tggagttggt gttgg                                         265
```

```
<210> SEQ ID NO 17
<211> LENGTH: 264
<212> TYPE: DNA
<213> ORGANISM: Macaca fascicularis
<220> FEATURE:
<221> NAME/KEY: misc_feature
<223> OTHER INFORMATION: Incyte ID No: 700710954H1

<400> SEQUENCE: 17
acttccgcag ccaggcaagc tgactgaggc cttcaagtac ttcctgcaag gcatgggcta    60
catggcctca tcctgcatga ctcgcctgtc ccggtctcgt acggcctctc taaccagtgc   120
agcatccatt gatggcaacc ggtcccgctc tcgcaccctg tctcagagca gcgagtctgg   180
aactctttct tcggggcccc cggtgcacac catggaggtc tcctgttgaa tgaccttgt    240 tgccctagtg tgggacccag ccct                                          264
```

```
<210> SEQ ID NO 18
<211> LENGTH: 240
<212> TYPE: DNA
<213> ORGANISM: Macaca fascicularis
<220> FEATURE:
<221> NAME/KEY: misc_feature
<223> OTHER INFORMATION: Incyte ID No: 700707576H1

<400> SEQUENCE: 18
ctgtcccggt ctcgtacggc ctctctaacc agtgcagcat ccattgatgg caaccggtcc    60
cgctctcgca ccctgtctca gagcagcgag tctggaactc tttcttcggg gccccgggg   120 cacaccagga ggtctcctgt tgaatgaccc ttgttgccct agtgtgggac ccagccctca   180
cctcccccag aactaacctg ggaggtgctg aaggggcatt gggccagagt aagcaaggga   240
```

```
<210> SEQ ID NO 19
<211> LENGTH: 264
<212> TYPE: DNA
<213> ORGANISM: Macaca fascicularis
<220> FEATURE:
<221> NAME/KEY: misc_feature
<223> OTHER INFORMATION: Incyte ID No: 700715158H1
```

<400> SEQUENCE: 19

| | |
|---|---|
| ggcagcggct gcagcaggca tcatggcgga ctgcaggagg tgcagatcac agaggagaag | 60 |
| ccactgctgc caggacagac gcctgaggcg gccaagattc actctgtgga gacaccgtat | 120 |
| ggctctgtca ctttcactgt ctatggcacc cccaaaccca aacgcccagc gatccttacc | 180 |
| taccacgatg tgggactcaa ctataaatct tgcttccagc cactgtttca attcggggac | 240 |
| atgcaggaaa tcattcagaa cttc | 264 |

<210> SEQ ID NO 20
<211> LENGTH: 329
<212> TYPE: DNA
<213> ORGANISM: Macaca fascicularis
<220> FEATURE:
<221> NAME/KEY: misc_feature
<223> OTHER INFORMATION: Incyte ID No: 700705541H1

<400> SEQUENCE: 20

| | |
|---|---|
| tgcactccaa actggacccg accaccacga ccttcctgaa gatggcagac tccggagggc | 60 |
| tgccccaggt cacacagcca gggaagctga ctgaagcctt caaatacttc ctgcaaggca | 120 |
| tgggctacat gccctcagcc agcatgaccc gcctggcacg ctcacgcact gcatccctca | 180 |
| ccagtgccag ctcggtggat ggcagccgcc acaggcctg cacccactcg gagagcagcg | 240 |
| aggggctggg ccaggtcaac cacaccatgg aggtgtcctg ttgaagccct cgatcccgct | 300 |
| gacgacgccc acctgtccgc ccacgtcga | 329 |

<210> SEQ ID NO 21
<211> LENGTH: 131
<212> TYPE: DNA
<213> ORGANISM: Macaca fascicularis
<220> FEATURE:
<221> NAME/KEY: misc_feature
<223> OTHER INFORMATION: Incyte ID No: 700719804H1

<400> SEQUENCE: 21

| | |
|---|---|
| agcggacggc tgcagcagac cccagagtca ggagtgagaa cgctgacccc taatcccact | 60 |
| gcatccagcc aataggagcc cagtaagtga ccccacctcg caggctgcag gctccttcct | 120 |
| gtgcaggcat c | 131 |

<210> SEQ ID NO 22
<211> LENGTH: 642
<212> TYPE: DNA
<213> ORGANISM: Canis familiaris
<220> FEATURE:
<221> NAME/KEY: misc_feature
<223> OTHER INFORMATION: Incyte ID No: 702769047H1

<400> SEQUENCE: 22

| | |
|---|---|
| ggcgggaccg gttgccatca atggacgccg cactggtcag cgaggccgtg cgcgatcgcg | 60 |
| acaggcgagt catgcaggac gaggccatgt agcccatgcc ttgcaggaag tacttgaagg | 120 |
| cctcggtcag cttgcctggc tgcgtcagct ggggctgacc tccagagtcg gccatcttga | 180 |
| gaaagaggt ctgggtgggg tccagctttg agttacactc caccactgca tcttcatggg | 240 |
| gtgcttggtc tccaccacc agcatcacag ggcacctgag ggtgacggca ccgccacgct | 300 |
| ccaggttcag gtctcggcga ttgttgtagc tgttccagta cagttcaatg ttctccaggt | 360 |
| tgggcgcatg tgtgatgatg tttctgtact tctgtatcag ctccgagttt ccagacagct | 420 |
| cctcctggct gaaaagatgt ccgaggatca tctccggaat ggaagaggtg agacctgtta | 480 |

| | |
|---|---|
| gcttgtgggc cgcccagtcc atccaaccct tggcattggg atcaatgttg atgaggacaa | 540 |
| gcccctcgac tgtatccggg tgggtcagag catatcgtga caggatgtag gctcagctcc | 600 |
| aacaccaact ccaattattg tggagaaatt caggtactgc ag | 642 |

<210> SEQ ID NO 23
<211> LENGTH: 651
<212> TYPE: DNA
<213> ORGANISM: Canis familiaris
<220> FEATURE:
<221> NAME/KEY: misc_feature
<223> OTHER INFORMATION: Incyte ID No: 702763624H1

<400> SEQUENCE: 23

| | |
|---|---|
| ctcggtcagc ttgcctggct gcgtcagctg gggctgacct ccagagtcgg ccatcttgag | 60 |
| aaaagaggtc tgggtggggt ccagctttga gttacactcc accactgcat cttcatgggg | 120 |
| tgcttggtct cccaccacca gcatcacagg gcacctgagg gtgacggcac cgccacgctc | 180 |
| caggttcagg tctcggcgat tgttgtagct gttccagtac agttcaatgt tctccaggtt | 240 |
| gggcgcatgt gtgatgatgt ttctgtactt ctgtatcagc tccgagtttc cagacagctc | 300 |
| ctcctggctg aaaagatgtc cgaggatcat ctccggaatg aagaggtga gacctgttag | 360 |
| cttgtgggcc gcccagtcca tccaacccct ggcattggga tcaatgttga tgaggacaag | 420 |
| cccctcgact gtatccgggt gggtcagagc atatcgtgac aggatgtagg ctccagctcc | 480 |
| aacaccaact ccaattattg tggagaaatt caggtactgc agaatgcaag ggatcatgtc | 540 |
| cgcgagctgg tccagagacg ggtactgata ccccaaaggg aacacgggag cccctcttcc | 600 |
| attccaggcg catccacatg aaccgcacga agtctgaatg atttctgcat g | 651 |

<210> SEQ ID NO 24
<211> LENGTH: 692
<212> TYPE: DNA
<213> ORGANISM: Canis familiaris
<220> FEATURE:
<221> NAME/KEY: misc_feature
<223> OTHER INFORMATION: Incyte ID No: 702776664H1

<400> SEQUENCE: 24

| | |
|---|---|
| ctgtactgga acagctacaa caatcgccga gacctgaacc tggagcgtgg cggtgccgtc | 60 |
| accctcaggt gccctgtgat gctggtggtg ggagaccaag caccccatga agatgcagtg | 120 |
| gtggagtgta actcaaagct ggaccccacc cagacctctt ttctcaagat ggccgactct | 180 |
| ggaggtcagc cccagctgac gcagccaggc aagctgaccg aggccttcaa gtacttcctg | 240 |
| caaggcatgg gctacatggc ctcgtcctgc atgactcgcc tgtcgcgatc gcgcacggcc | 300 |
| tcgctgacca gtgcggcgtc cattgatggc aaccggtccc gctcccgcac cctgtcgcag | 360 |
| ggcagcgagt ctgggactct cccttcaggg ccgccaggac ataccatgga ggtctcctgc | 420 |
| tgaatggcct cggttgccct gctcaccgga cccagccctc acctccgcct gcactaacct | 480 |
| gggaggtcct aggcgctgg gccagagtaa gggaggacgg gtggatcatg tggggagatg | 540 |
| accttgatct ttgattgcta ccctaaactt gactctaacc tgtgattccc ctcagctcct | 600 |
| gagagatgcc ctaatatcta gatattagga cagatgtcta aatatctctt agggacccag | 660 |
| accctaaaatt atcctctctt cagatctctg aa | 692 |

<210> SEQ ID NO 25
<211> LENGTH: 633
<212> TYPE: DNA
<213> ORGANISM: Canis familiaris

```
<220> FEATURE:
<221> NAME/KEY: misc_feature
<223> OTHER INFORMATION: Incyte ID No: 702778279H1
<221> NAME/KEY: unsure
<222> LOCATION: 364-404
<223> OTHER INFORMATION: a, t, c, g, or other

<400> SEQUENCE: 25
gcagatcaca gaggagaagc cgctgttgcc aggcagacgc ccgagacggc caaggttatg      60
agacccttg  accgactccc aggcccgagt tccagacctg caggcatccc ctcgcctcct     120
gccgccccaa atccataatc tcattctaat ccgcacccat gttttctcca cctgaccca     180
cgtctctctc cccgccgccg ccacgggagt ccaggcctgt gccccgtcac tgcactaacc     240
ttcatcctct tcatgtctct ttgtcatctc tttctgtctc ttgtcttggt cttttgccc     300
acctgtcatt gtctgtgtct gtctctccat ctgtgactac acggctgtgt gtctctgtgc     360
atannnnnnn nnnnnnnnnn nnnnnnnnnn nnnnnnnnnn nnnnccagga ggctgagtta     420
gctgcccgaa tcctcctgga ccggggacag actcactctg tggagacacc gtatggctct     480
gtcactttta ctgtctatgg gaccccaag cccaaacgcc cagcgatact cacctaccat     540
gatgtaggac tcaactataa gtcttgcttc cagccgctct ttcagttcgg ggacatgcag     600
gaaatcattc agaacttcgt gcggttcatg tgg                                  633

<210> SEQ ID NO 26
<211> LENGTH: 461
<212> TYPE: DNA
<213> ORGANISM: Canis familiaris
<220> FEATURE:
<221> NAME/KEY: misc_feature
<223> OTHER INFORMATION: Incyte ID No: 702249907H1

<400> SEQUENCE: 26
gagggcacgt gtcccctctc cctaatctag gtgtccatag ataagggata agaggttgtg      60
gtagtcgtcc catggtgccc ccaccagact ctccctgctt accccactgc aaggggaggg     120
gacttggggc tgggactcca ttcaccaaag ctgatatggc ttctcattaa cccttcagat     180
ctctgaagag tatgggccta aatgaatgtg tgtcagagaa ggcttgctgg tgggttagtg     240
gtcctcaggt tggggtagag acatccagtg tgtgaaacgg aagtcggaat ggtgggctgt     300
gaacaagtct gagggaagga tcagagctgg ggcaatagga aggggcctgg ggccattggc     360
tgcactaact ttggtagctg tgtagacagt gtgtgtctac agtgggaggg gagggagct     420
cagctgggac agggctgctt ggggcttggc gtaggggtgg g                         461

<210> SEQ ID NO 27
<211> LENGTH: 610
<212> TYPE: DNA
<213> ORGANISM: Rattus norvegicus
<220> FEATURE:
<221> NAME/KEY: misc_feature
<223> OTHER INFORMATION: Incyte ID No: 702025443H1

<400> SEQUENCE: 27
tgtcacgata cgctctgaac cacccggaca ccgttgaagg tcttgttctc atcaacattg      60
atcccaacgc caagggctgg atggattggg cagcccacaa gttaaccggc cttacgtctt     120
ccattccgga gatgattctt gggcaccttt tcagccagga agagctttct ggaaattctg     180
aattgataca gaagtataga agtctcatca cacacgcgcc caacctggag aacatcgaac     240
tgtattggaa cagttacaac aaccgccgag acctgaactt tgagcgaggt ggtgagatga     300
```

-continued

| cctcaagtg ccccgtgatg ctggtggtag gagaccaagc acctcatgaa gatgccgtgg | 360 |
| tggaatgtaa ttcaaaactg gacccacac agacctcatt cctcaagatg gcggactctg | 420 |
| gaggtcagcc gcagctgact cagccaggca agctgacaga agctttcaag tacttcgtgc | 480 |
| aaggcatggg ctacatggcc tcatcctgta tgactcgcct gtctcggtct cgcacagcat | 540 |
| ctctgaccag tgcggatcca tcgatggcag tcggtcccga tcccgcaccc tgtcgcagag | 600 |
| tagcgagtct | 610 |

<210> SEQ ID NO 28
<211> LENGTH: 533
<212> TYPE: DNA
<213> ORGANISM: Rattus norvegicus
<220> FEATURE:
<221> NAME/KEY: misc_feature
<223> OTHER INFORMATION: Incyte ID No: 702028546H2

<400> SEQUENCE: 28

| atgatgtagg actcaactat aaatcttgct tccagccact gtttcagttc ggggatatgc | 60 |
| aagagatcat acagaacttc gtgcgggtcc atgtggatgc ccctggaatg gaagagggg | 120 |
| cacctgtgtt tcctctgggg taccagtacc atctctggga ccagcttgca gacatgattc | 180 |
| cttgcatcct gcagtactta aatttctcta cgataattgg agttggcgtt ggagctggag | 240 |
| catacattct gtcacgatac gctctgaacc accggacac cgttgaaggt cttgttctca | 300 |
| tcaacattga tcccaacgcc aagggctgga tggattgggc agcccacaag ttaaccggcc | 360 |
| ttacgtcttc cattccggag atgattcttg gcaccttttt cagccaggaa gagctttctg | 420 |
| gaaattctga attgatacag aagtatagaa gtctcatcac acacgcgccc aacctggaga | 480 |
| acatcgaact gtattggaac agttacaaca accgccgaga cctgaacttt gag | 533 |

<210> SEQ ID NO 29
<211> LENGTH: 540
<212> TYPE: DNA
<213> ORGANISM: Rattus norvegicus
<220> FEATURE:
<221> NAME/KEY: misc_feature
<223> OTHER INFORMATION: Incyte ID No: 702160576H1

<400> SEQUENCE: 29

| gccactgttg ccaggacaga cgcctgaggc tgccaagact cattctgtgg agacacctta | 60 |
| tggctccgtc acttttaccg tgtatggcac ccccaaaccc aaacgtccag cgatattcac | 120 |
| ctaccatgat gtaggactca actataaatc ttgcttccag ccactgtttc agttcgggga | 180 |
| tatgcaagag atcatacaga acttcgtgcg ggtccatgtg gatgcccctg gaatggaaga | 240 |
| gggggcacct gtgtttcctc tggggtacca gtacccatct ctggaccagc ttgcagacat | 300 |
| gattccttgc atcctgcagt acttaaattt ctctacgata attggagttg gcgttggagc | 360 |
| tggagcatac attctgtcac gatacgctct gaaccacccg acaccgttg aaggtcttgt | 420 |
| tctcatcaac attgatccca acgccaaggg ctggatggat tgggcagccc acaagttaac | 480 |
| cggccttacg tcttccattc cggagatgat tcttgggcac cttttcagcc aggaagagct | 540 |

<210> SEQ ID NO 30
<211> LENGTH: 489
<212> TYPE: DNA
<213> ORGANISM: Rattus norvegicus
<220> FEATURE:
<221> NAME/KEY: misc_feature
<223> OTHER INFORMATION: Incyte ID No: 701938896H1

-continued

```
<400> SEQUENCE: 30
cccgaatcct cctggaccag gacagactca ttctgtggag acaccttatg gctccgtcac       60
ttttaccgtg tatggcaccc cctaacccaa acgtccagcg atattcaact aacaaggatg      120
taggactcaa ctataaatct tgcttccagc cactgtttca gttcggggat atgcaagaga      180
tcatacagaa cttcgtgcgg gtccatgtgg atgcccctgg aatggaagag ggggcacctg      240
tgtttcctct ggggtaccag tacccatctc tggaccagct tgcagacatg attccttgca      300
tcctgcagta cttaaatttc tctacgataa ttggagttgg cgttggagct ggagcataca      360
ttctgtcacg atacgctctg aaccacccgg acaccgttga aggtcttgtt ctcatcaaca      420
ttgatcccaa cgccaagggc tggatggatt gggcagccca aagttaacc gggcttacgt       480 cttccattc                                                              489

<210> SEQ ID NO 31
<211> LENGTH: 317
<212> TYPE: DNA
<213> ORGANISM: Rattus norvegicus
<220> FEATURE:
<221> NAME/KEY: misc_feature
<223> OTHER INFORMATION: Incyte ID No: 701646914H1

<400> SEQUENCE: 31
gcggctgcag caggccacca tggcagagct tcaggaggtg cagatcactg aggagaagcc       60
actgttgcca ggacagacgc ctgaggctgc caaggaggct gagttagctg cccgaatcct      120
cctggaccag ggacagactc attctgtgga gacaccttat ggctccgtca cttttaccgt      180
gtatggcacc cccaaaccca tacgtccagc gatattcacc taccatgatg taggactcaa      240
ctataaatct tgcttccagc cactgtttca gttcggggat atgcaagaga tcatacagaa      300
cttcgtgcgg gtccatg                                                     317

<210> SEQ ID NO 32
<211> LENGTH: 371
<212> TYPE: PRT
<213> ORGANISM: Mus musculus
<220> FEATURE:
<221> NAME/KEY: misc_feature
<223> OTHER INFORMATION: GenBank ID No: g6141566

<400> SEQUENCE: 32

Met Ala Glu Leu Gln Glu Val Gln Ile Thr Glu Glu Lys Pro Leu
  1               5                  10                  15

Leu Pro Gly Gln Thr Pro Glu Thr Ala Lys Glu Ala Glu Leu Ala
                 20                  25                  30

Ala Arg Ile Leu Leu Asp Gln Gly Gln Thr His Ser Val Glu Thr
                 35                  40                  45

Pro Tyr Gly Ser Val Thr Phe Thr Val Tyr Gly Thr Pro Lys Pro
                 50                  55                  60

Lys Arg Pro Ala Ile Phe Thr Tyr His Asp Val Gly Leu Asn Tyr
                 65                  70                  75

Lys Ser Cys Phe Gln Pro Leu Phe Arg Phe Gly Asp Met Gln Glu
                 80                  85                  90

Ile Ile Gln Asn Phe Val Arg Val His Val Asp Ala Pro Gly Met
                 95                 100                 105

Glu Glu Gly Ala Pro Val Phe Pro Leu Gly Tyr Gln Tyr Pro Ser
                110                 115                 120

Leu Asp Gln Leu Ala Asp Met Ile Pro Cys Ile Leu Gln Tyr Leu
```

-continued

```
                    125                 130                 135

Asn Phe Ser Thr Ile Ile Gly Val Gly Val Gly Ala Gly Ala Tyr
                    140                 145                 150

Ile Leu Ser Arg Tyr Ala Leu Asn His Pro Asp Thr Val Glu Gly
                    155                 160                 165

Leu Val Leu Ile Asn Ile Asp Pro Asn Ala Lys Gly Trp Met Asp
                    170                 175                 180

Trp Ala Ala His Lys Leu Thr Gly Leu Thr Ser Ser Ile Pro Asp
                    185                 190                 195

Met Ile Leu Gly His Leu Phe Ser Gln Glu Leu Ser Gly Asn
                    200                 205                 210

Ser Glu Leu Ile Gln Lys Tyr Arg Gly Ile Ile Gln His Ala Pro
                    215                 220                 225

Asn Leu Glu Asn Ile Glu Leu Tyr Trp Asn Ser Tyr Asn Asn Arg
                    230                 235                 240

Arg Asp Leu Asn Phe Glu Arg Gly Gly Glu Thr Thr Leu Lys Cys
                    245                 250                 255

Pro Val Met Leu Val Val Gly Asp Gln Ala Pro His Glu Asp Ala
                    260                 265                 270

Val Val Glu Cys Asn Ser Lys Leu Asp Pro Thr Gln Thr Ser Phe
                    275                 280                 285

Leu Lys Met Ala Asp Ser Gly Gly Gln Pro Gln Leu Thr Gln Pro
                    290                 295                 300

Gly Lys Leu Thr Glu Ala Phe Lys Tyr Phe Leu Gln Gly Met Gly
                    305                 310                 315

Tyr Met Ala Ser Ser Cys Met Thr Arg Leu Ser Arg Ser Arg Thr
                    320                 325                 330

Ala Ser Leu Thr Ser Ala Ala Ser Ile Asp Gly Ser Arg Ser Arg
                    335                 340                 345

Ser Arg Thr Leu Ser Gln Ser Ser Glu Ser Gly Thr Leu Pro Ser
                    350                 355                 360

Gly Pro Pro Gly His Thr Met Glu Val Ser Cys
                    365                 370
```

<210> SEQ ID NO 33
<211> LENGTH: 394
<212> TYPE: PRT
<213> ORGANISM: Homo sapiens
<220> FEATURE:
<221> NAME/KEY: misc_feature
<223> OTHER INFORMATION: GenBank ID No: g1596167

<400> SEQUENCE: 33

```
Met Ser Arg Glu Met Gln Asp Val Asp Leu Ala Glu Val Lys Pro
  1                 5                  10                  15

Leu Val Glu Lys Gly Glu Thr Ile Thr Gly Leu Leu Gln Glu Phe
                    20                  25                  30

Asp Val Gln Glu Gln Asp Ile Glu Thr Leu His Gly Ser Val His
                    35                  40                  45

Val Thr Leu Cys Gly Thr Pro Lys Gly Asn Arg Pro Val Ile Leu
                    50                  55                  60

Thr Tyr His Asp Ile Gly Met Asn His Lys Thr Cys Tyr Asn Pro
                    65                  70                  75

Leu Phe Asn Tyr Glu Asp Met Gln Glu Ile Thr Gln His Phe Ala
                    80                  85                  90
```

-continued

```
Val Cys His Val Asp Ala Pro Gly Gln Asp Gly Ala Ala Ser
             95                 100                 105

Phe Pro Ala Gly Tyr Met Tyr Pro Ser Met Asp Gln Leu Ala Glu
            110                 115                 120

Met Leu Pro Gly Val Leu Gln Gln Phe Gly Leu Lys Ser Ile Ile
            125                 130                 135

Gly Met Gly Thr Gly Ala Gly Ala Tyr Ile Leu Thr Arg Phe Ala
            140                 145                 150

Leu Asn Asn Pro Glu Met Val Glu Gly Leu Val Leu Ile Asn Val
            155                 160                 165

Asn Pro Cys Ala Glu Gly Trp Met Asp Trp Ala Ala Ser Lys Ile
            170                 175                 180

Ser Gly Trp Thr Gln Ala Leu Pro Asp Met Val Val Ser His Leu
            185                 190                 195

Phe Gly Lys Glu Glu Met Gln Ser Asn Val Glu Val Val His Thr
            200                 205                 210

Tyr Arg Gln His Ile Val Asn Asp Met Asn Pro Gly Asn Leu His
            215                 220                 225

Leu Phe Ile Asn Ala Tyr Asn Ser Arg Arg Asp Leu Glu Ile Glu
            230                 235                 240

Arg Pro Met Pro Gly Thr His Thr Val Thr Leu Gln Cys Pro Ala
            245                 250                 255

Leu Leu Val Val Gly Asp Ser Ser Pro Ala Val Asp Ala Val Val
            260                 265                 270

Glu Cys Asn Ser Lys Leu Asp Pro Thr Lys Thr Thr Leu Leu Lys
            275                 280                 285

Met Ala Asp Cys Gly Gly Leu Pro Gln Ile Ser Gln Pro Ala Lys
            290                 295                 300

Leu Ala Glu Ala Phe Lys Tyr Phe Val Gln Gly Met Gly Tyr Met
            305                 310                 315

Pro Ser Ala Ser Met Thr Arg Leu Met Arg Ser Arg Thr Ala Ser
            320                 325                 330

Gly Ser Ser Val Thr Ser Leu Asp Gly Thr Arg Ser Arg Ser His
            335                 340                 345

Thr Ser Glu Gly Thr Arg Ser Arg Ser His Thr Ser Glu Gly Thr
            350                 355                 360

Arg Ser Arg Ser His Thr Ser Glu Gly Ala His Leu Asp Ile Thr
            365                 370                 375

Pro Asn Ser Gly Ala Ala Gly Asn Ser Ala Gly Pro Lys Ser Met
            380                 385                 390

Glu Val Ser Cys
```

NDR2-RELATED PROTEINS

This application is a continuation-in-part of copending U.S. Ser. No. 09/232,160, filed Jan. 15, 1999, all of which application is hereby incorporated by reference.

FIELD OF THE INVENTION

This invention relates to cDNAs which encode Ndr2-related proteins and to the use of the cDNAs and the encoded proteins in the diagnosis and treatment of cancer, particularly cancers of the intestine, breast, uterus, liver, brain, and kidney.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

Reducing agents and tunicamycin-responsive protein (RTP; also referred to as Drg1, Cap43, and rit43) may play roles in atherosclerosis, tumorigenesis, differentiation, hypoxia, and cellular responses to stress (Agarwala et al. (2000) Biochem Biophys Res Commun 272:641–647). Human RTP is a 43 kDa cytoplasmic protein of 394 amino acids in length and is expressed ubiquitously. Although RTP is present predominantly in the cytoplasm of cells, immunofluorescence studies show that a fraction of RTP is located in the nucleus, an indication that RTP may be a signaling protein that shuttles between the cytoplasm and nucleus. The expression level of RTP increases in response to various chemical compounds, including homocysteine, cysteine, mercaptoethanol, tunicamycin, lysophosphatidylcholine, nickel compounds, okadaic acid, calcium ionophore, DNA-damaging agents, 1,25-(OH)$_2$ vitamin D3, synthetic retinoids, and phorbol myristate acetate. RTP expression is decreased in tumor cell lines and in colon, breast and prostate tumors (Kurdistani et al. (1998) Cancer Res 58:4439–4444; van Belzen et al. (1997) Lab Invest 77:85–92). Overexpression of RTP inhibits the growth of cancerous cells. RTP expression is upregulated in human myelomonocytic cells by retinoids that inhibit proliferation and promote differentiation (Piquemal et al. (1999) Biochim Biophys Acta 1450:364–373) and in prostate adenocarcionma cells by androgens that induce differentiation (Ulrix et al. (1999) FEBS Lett 455:23–26). The activity of RTP may be regulated by phosphorylation. RTP is phosphorylated in vivo by an unknown kinase at multiple sites and can be phosphorylated by protein kinase A in vitro (Agarwala et al., supra). RTP is dephosphorylated in cells exposed to homocysteine. RTP expression levels change at different stages of the cell cycle. RTP expression is highest at the G1 and G2-M stages and lower at S phase (Kurdistani et al., supra). The transcription factor p53, a known tumor suppressor, induces expression of RTP. P53 causes the arrest of cell growth at G1 and G2, and RTP may play a role in this growth-arrest pathway.

Mouse Ndr1 is a homolog of RTP that was identified in a screen for genes regulated by N-myc. Ndr1 shows increased expression in N-myc deficient mice (Okuda and Kondoh (1999) Mech Dev 83:39–52). Myc family transcription factors control genes expressed during embryogenesis, proliferation, differentiation, apoptosis, and tumorigenesis (Grandori et al. (2000) Annu Rev Cell Dev Biol 16:653–699). N-myc expression is high during cell proliferation and decreased during cell differentiation. Rearrangements and mutations of Myc proteins are found in many tumors. N-Myc represses transcription of Ndr1. During mouse embryogenesis, Ndr1 expression is correlated with a decrease in N-myc expression and Ndr1 levels increase when cells begin to differentiate. Ndr1 appears, therefore, to be a signaling molecule involved in cellular differentiation.

Two Ndr1-related genes, Ndr2 and Ndr3, have recently been discovered (Okuda and Kondoh (1999) Biochem and Biophys Res Commun 266:208–215). The amino acid sequences of Ndr2 and Ndr3 proteins show 54% and 64% identity to Ndr1, respectively, and therefore are grouped with Ndr1 as the Ndr family. All three Ndr genes are expressed during embryogenesis, but at different times and show differences in the regulation of their expression levels. Unlike Ndr1, Ndr2 expression is not upregulated in N-myc deficient mouse embryos. Ndr1 expression, in mouse embryos, increases after 13.5 dpc whereas Ndr2 expression increases earlier, at 11.5 dpc, and Ndr3 expression is high at 9.5 dpc and shows little increase at later developmental stages. RTP, Ndr1, Ndr2, and Ndr3 may represent a gene family with differentiation-related functions.

The discovery of cDNAs encoding Ndr2-related proteins satisfies a need in the art by providing compositions which are useful in the diagnosis and treatment of cancer, particularly cancers of the intestine, breast, uterus, liver, brain, and kidney.

SUMMARY OF THE INVENTION

The invention is based on the discovery of cDNAs encoding Ndr2-related proteins (NRP) which are useful in the diagnosis and treatment of cancer, particularly cancers of the intestine, breast, uterus, liver, brain, and kidney.

The invention provides an isolated cDNA comprising a nucleic acid sequence encoding a protein selected from the group consisting of the amino acid sequences of SEQ ID NO:1 (NRP1) and SEQ ID NO:2 (NRP2). The invention also provides an isolated cDNA or the complement thereof selected from the group consisting of the nucleic acid sequences of SEQ ID NO:3 and SEQ ID NO:11, a fragment of SEQ ID NO:3 selected from SEQ ID NOs:4–10 or a fragment of SEQ ID NO:11 selected from SEQ ID NOs:12–15, and a variant of SEQ ID NO:3 or SEQ ID NO:11 selected from SEQ ID NOs:16–31. The invention additionally provides a composition, a substrate, and a probe comprising the cDNA, or the complement of the cDNA, encoding NRP. The invention further provides a vector containing the cDNA, a host cell containing the vector and a method for using the cDNA to make NRP. The invention still further provides a transgenic cell line or organism comprising the vector containing the cDNA encoding NRP. The invention additionally provides a fragment, a variant, or the complement of the cDNA selected from the group consisting of SEQ ID NOs:2–31. In one aspect, the invention provides a substrate containing at least one of these fragments or variants or the complements thereof. In a second aspect, the invention provides a probe comprising a cDNA or the complement thereof which can be used in methods of detection, screening, and purification. In a further aspect, the probe is a single-stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose cancer, particularly cancers of the intestine, breast, uterus, liver, brain, and kidney. In another aspect, the cDNA or a fragment or a variant or the complements thereof may comprise an element on an array.

The invention additionally provides a method for using a cDNA or a fragment or a variant or the complements thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified protein or a portion thereof selected from the group consisting of an amino acid sequence of SEQ ID NO:1 or SEQ ID NO:2, a variant having at least 97% identity to the amino acid sequence of SEQ ID NO:1 or SEQ ID NO:2, an antigenic epitope of SEQ ID NO:1 or SEQ ID NO:2, and a biologically active portion of SEQ ID NO:1 or SEQ ID NO:2. The invention also provides a composition comprising the purified protein in conjunction with a pharmaceutical carrier. The invention further provides a method of using the NRP to treat a subject with cancer, particularly cancers of the intestine, breast, uterus, liver, brain, and kidney comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with cancer, particularly cancers of the intestine, breast, uterus, liver, brain, and kidney.

The invention provides a method of using a protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of cancer, particularly cancers of the intestine, breast, uterus, liver, brain, and kidney.

The invention also provides a method of using a protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, dissociating the antibodies from the protein, thereby obtaining purified antibodies.

The invention provides a purified antibody which binds specifically to a protein which is expressed in cancer, particularly cancers of the intestine, breast, uterus, liver, brain, and kidney. The invention also provides a method of using an antibody to diagnose cancer, particularly cancers of the intestine, breast, uterus, liver, brain, and kidney comprising combining the antibody comparing the quantity of bound antibody to known standards, thereby establishing the presence of cancer, particularly cancers of the intestine, breast, uterus, liver, brain, and kidney. The invention further provides a method of using an antibody to treat cancer, particularly cancers of the intestine, breast, uterus, liver, brain, and kidney comprising administering to a patient in need of such treatment a pharmaceutical composition comprising the purified antibody.

The invention provides a method for inserting a heterologous marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:3–31, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A, 1B, 1C, 1D, 1E, 1F, and 1G show the NRP (SEQ ID NO:1) encoded by the cDNA (SEQ ID NO:3). The translation was produced using MACDNASIS PRO software (Hitachi Software Engineering, South San Francisco Calif.).

FIGS. 2A, 2B, 2C, 2D, 2E, 2F, and 2G show the NRP (SEQ ID NO:2) encoded by the cDNA (SEQ ID NO:11). The translation was produced using MACDNASIS PRO software (Hitachi Software Engineering).

Figure 3B:
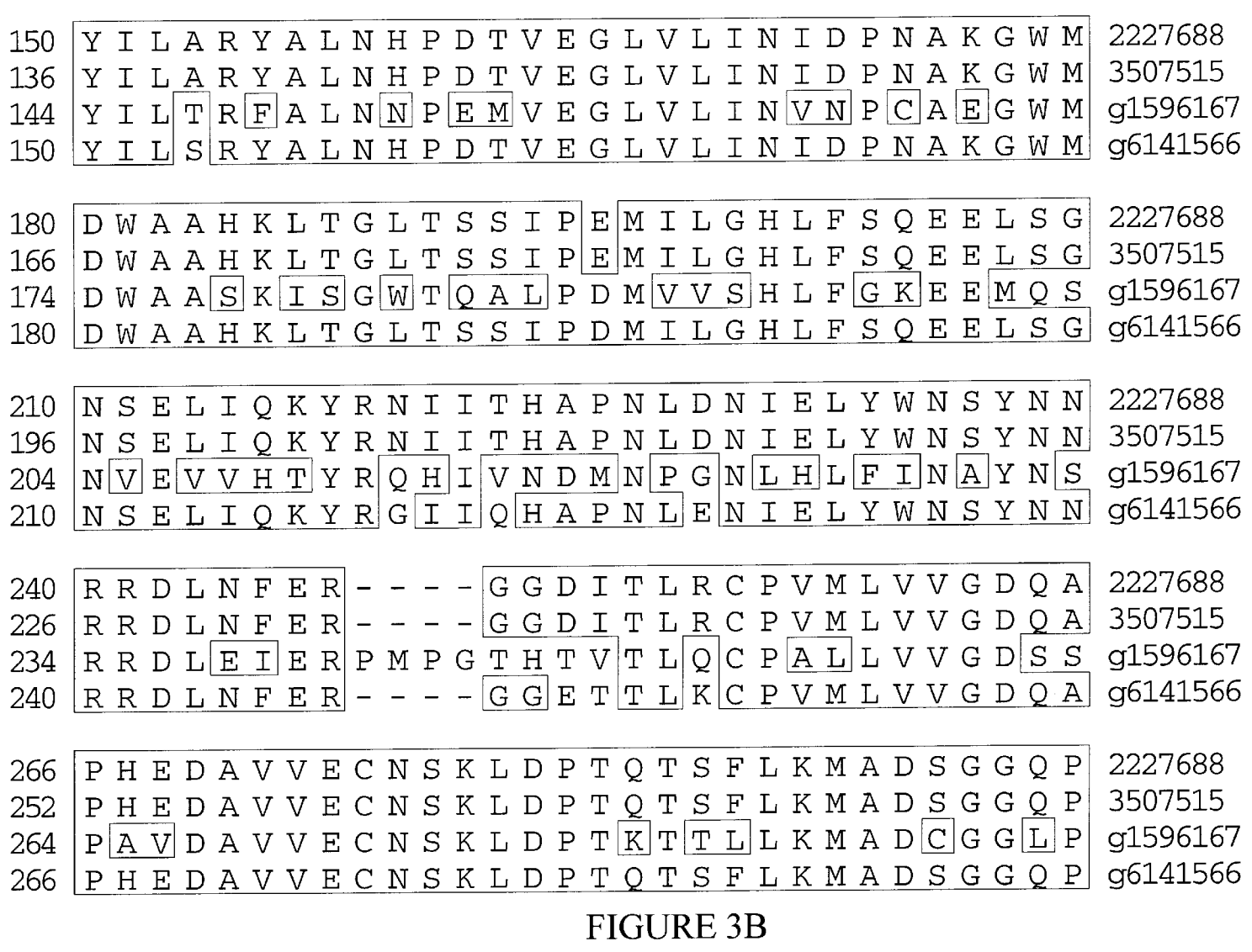

FIGS. 3A, 3B, and 3C demonstrate the conserved chemical and structural similarities among the sequences and domains of NRP1 (2227688; SEQ ID NO:1), NRP2 (3507515; SEQ ID NO:2), mouse Ndr2 (g6141566; SEQ ID NO:32), and human RTP (g1596167; SEQ ID NO:33). The alignment was produced using the MEGALIGN program of LASERGENE software (DNASTAR, Madison Wis.).

Tables 1 and 2 show the northern analysis for NRP produced using the LIFESEQ Gold database (Incyte Genomics, Palo Alto Calif.). In Table 1, the first column presents the tissue categories; the second column, the total number of clones in the tissue category; the third column, the ratio of the number of libraries in which at least one transcript was found to the total number of libraries; the fourth column, absolute clone abundance of the transcript; and the fifth column, percent abundance of the transcript. Table 2 shows expression of NRP in intestine, breast, uterus, liver, brain, and kidney tissues, particularly from patients with cancer. The first column lists the library name, the second column, the number of clones sequenced for that library; the third column, the description of the tissue from which the library was derived; the fourth column, the absolute abundance of the transcript; and the fifth column, the percent abundance of the transcript.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"NRP" refers to a purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard, and the other, a cDNA of diagnostic or therapeutic interest. The arrangement of from about two to about 40,000 cDNAs on the substrate assures that the size and signal intensity of each labeled hybridization complex formed between each cDNA and at least one sample nucleic acid is individually distinguishable.

The "complement" of a cDNA of the Sequence Listing refers to a nucleic acid molecule which is completely complementary over its full length and which will hybridize to the cDNA or an mRNA under conditions of maximal stringency.

"cDNA" refers to an isolated polynucleotide, nucleic acid molecule, or any fragment or complement thereof. It may have originated recombinantly or synthetically, may be double-stranded or single-stranded, represents coding and noncoding 3' or 5' sequence, and generally lacks introns.

The phrase "cDNA encoding a protein" refers to a nucleotide sequence that closely aligns with sequences which encode conserved regions, motifs or domains that were identified by employing analyses well known in the art. These analyses include BLAST (Basic Local Alignment Search Tool) which provides identity within the conserved region (Altschul (1993) J Mol Evol 36: 290–300; Altschul et al. (1990) J Mol Biol 215:403–410).

A "composition" comprises the polynucleotide and a labeling moiety or a purified protein in conjunction with a pharmaceutical carrier.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alky, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by presence, absence or at least two-fold changes in the amount of transcribed messenger RNA or translated protein in a sample.

"Disorder" refers to conditions, diseases or syndromes in which the cDNAs and NRP are differentially expressed. Such a disorder includes cancer, particularly cancers of the intestine, breast, uterus, liver, brain, and kidney.

"Fragment" refers to a chain of consecutive nucleotides from about 50 to about 4000 base pairs in length. Fragments may be used in PCR or hybridization technologies to identify related nucleic acid molecules and in binding assays to screen for a ligand. Such ligands are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. Hybridization conditions, degree of complementarity and the use of nucleotide analogs affect the efficiency and stringency of hybridization reactions.

"Labeling moiety" refers to any visible or radioactive label than can be attached to or incorporated into a cDNA or protein. Visible labels include but are not limited to anthocyanins, green fluorescent protein (GFP), β glucuronidase, luciferase, Cy3 and Cy5, and the like. Radioactive markers include radioactive forms of hydrogen, iodine, phosphorous, sulfur, and the like.

"Ligand" refers to any agent, molecule, or compound which will bind specifically to a polynucleotide or to an epitope of a protein. Such ligands stabilize or modulate the activity of polynucleotides or proteins and may be composed of inorganic and/or organic substances including minerals, cofactors, nucleic acids, proteins, carbohydrates, fats, and lipids.

"Oligonucleotide" refers a single-stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single-stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte- Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated.

"Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them. Particularly in proteins, similarity is greater than identity in that conservative substitutions, for example, valine for leucine or isoleucine, are counted in calculating the reported percentage. Substitutions which are considered to be conservative are well known in the art.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

The Invention

The invention is based on the discovery of cDNAs which encode NRP and on the use of the cDNAs, or fragments thereof, and proteins, or portions thereof, directly or as compositions in the characterization, diagnosis, and treatment of cancer, particularly cancers of the intestine, breast, uterus, liver, brain, and kidney. NRP1 and NRP2 of the present invention were discovered as genes that regulate cell proliferation by their differential expression in noncancerous, precancerous, and cancerous tissues. The identification and characterization of the cDNAs and proteins, fragments or portions thereof, were described in U.S. Ser. No. 09/232,160.

Nucleic acids encoding the NRP1 of the present invention were first identified in Incyte Clone 2227688 from the seminal vesicle cDNA library (SEMVNOT01) using a computer search for nucleotide and/or amino acid sequence alignments. SEQ ID NO:3 was derived from the following overlapping and/or extended nucleic acid sequences (SEQ ID NO:4–10): Incyte Clones 2227688H1 (SEMVNOT01), 3507515H1 (CONCNOT01), 027805X7 (SPLNFET01), 1300824F1 (BRSTNOT07), 1384447F1 (BRAITUT08), 1291929T1 (PGANNOT03), and 1367779H1 (SCORNON02).

In one embodiment, the invention encompasses a polypeptide comprising the amino acid sequence of SEQ ID NO:1 as shown in FIGS. 1A, 1B, 1C, 1D, 1E, 1F, and 1G. NRP1 is 371 amino acids in length and has two potential N-glycosylation sites at N136 and N342; four potential casein kinase II phosphorylation sites at T67, S192, S203, and S276; two potential protein kinase C phosphorylation sites at T57 and T252; and one potential tyrosine kinase phosphorylation site at Y309. PFAM and PRINTS analyses indicate that the region of NRP1 from F95 to L311 is similar to an alpha-beta hydrolase fold. PRINTS analysis indicates that the region of NRP1 from F85 to P103 is similar to an androgen receptor signature. As shown in FIGS. 3A, 3B, and 3C, NRP1 has chemical and structural similarity with mouse Ndr2 (g6141566; SEQ ID NO:32), and human RTP (g1596167; SEQ ID NO:33). In particular, NRP1 and Ndr2 share about 96% identity. NRP1 and RTP share about 52% identity. NRP1, Ndr2, and RTP share a predicted alpha-beta hydrolase fold and an androgen receptor signature. Useful antigenic epitopes extend from about E11 to about R32, from about N238 to about R254, and from about S335 to about E368; and a biologically active portion of NRP1 extends from about 85 to about 103. An antibody which specifically binds NRP1 is useful in a diagnostic assay to identify cancer, particularly cancers of the intestine, breast, uterus, liver, brain, and kidney.

Nucleic acids encoding the NRP2 of the present invention were first identified in Incyte Clone 3507515 from the chest wall soft tissue cDNA library (CONCNOT01) using a computer search for nucleotide and/or amino acid sequence alignments. SEQ ID NO:11 was derived from the following overlapping and/or extended nucleic acid sequences (SEQ ID NO:12–15): Incyte Clones 3507515F6 (CONCNOT01), 1214191R1 (BRSTTUT01), 3364735F6 (PROSBPT02), and 1289617F1 (BRAINOT11).

In another embodiment, the invention encompasses a polypeptide comprising the amino acid sequence of SEQ ID NO:2 as shown in FIGS. 2A, 2B, 2C, 2D, 2E, 2F, and 2G. NRP2 is 402 amino acids in length and has one potential N-glycosylation site at N122; four potential casein kinase II phosphorylation sites at T53, S178, S189, and S262; three potential protein kinase C phosphorylation sites at T43, T238 and S398; and one potential tyrosine kinase phosphorylation site at Y295. PFAM and PRINTS analyses indicate that the region of NRP2 from F81 to L297 is similar to an alpha-beta hydrolase fold. PRINTS analysis indicates that the regions of NRP2 from F71 to P89 and from R350 to S370 are similar to an androgen receptor signature. As shown in FIGS. 3A, 3B, and 3C, NRP2 has chemical and structural similarity with mouse Ndr2 (g6141566; SEQ ID NO:32), and human RTP (g1596167; SEQ ID NO:33). In particular, NRP2 and Ndr2 share about 89% identity. NRP2 and RTP share about 49% identity. NRP2, Ndr2, and RTP share a predicted alpha-beta hydrolase fold and an androgen receptor signature. Useful antigenic epitopes extend from about Q8 to about S28, from about N221 to about R240, and from about N377 to about G401; and biologically active portions of NRP2 extend from about 71 to about 89 and from about 350 to about 370. An antibody which specifically binds NRP2 is useful in an diagnostic assay to identify cancer, particularly cancers of the intestine, breast, uterus, liver, brain, and kidney.

Table 1 shows expression of NRP1 and NRP2 across the tissue categories. NRP is expressed predominantly in the nervous system, exocrine glands, female reproductive tissue, and male reproductive tissue. Table 2 shows expression of NRP in intestine, breast, uterus, liver, brain, and kidney, particularly from patients with cancer. Libraries in which the transcript has an absolute abundance of more than one provide an indication of overexpression in these tissues. NRP is found in libraries associated with various cancers, in particular, a small intestine library (SINTTUT01) from a patient with ileum carcinoid, breast tumor libraries (BRSTTUP03 and BRSTTUT17) from patients with ductal carcinoma, a uterine tumor library (UTRSTUE01) from a patient with leiomyoma, a liver tumor library (LIVRTUT04) from a patient with hepatoma, a brain tumor library (BRAITUP04) from a patient with oligodendroglioma, a brain tumor library (BRAITUP06) from a patient with astrocytoma, and kidney tumor libraries (KIDNTUT13, KIDNTUP05, and KIDNTUE01) from patients with renal cell carcinoma. Therefore, the cDNAs encoding NRP1 or NRP2 are useful in assays to diagnose cancer, particularly cancers of the intestine, breast, uterus, liver, brain, and kidney. A fragment of the cDNA encoding NRP1 from about nucleotide 1 to about nucleotide 50 is also useful in diagnostic assays. A fragment of the cDNA encoding NRP2 from about nucleotide 1 to about nucleotide 50 is useful in diagnostic assays.

Mammalian variants of the cDNA encoding NRP were identified using BLAST2 with default parameters and the ZOOSEQ databases (Incyte Genomics). These preferred variants have from about 82% to about 97% identity as shown in the table below. The first column shows the SEQ ID for the human cDNA (SEQ ID$_H$); the second column, the SEQ ID for the variant cDNAs (SEQ ID$_{var}$); the third column, the clone number for the variant cDNAs (Clone$_{var}$); the fourth column, the library name; the fifth column, the alignment of the variant cDNA to the human cDNA; and the sixth column, the percent identity to the human cDNA.

| SEQ ID$_H$ | SEQ ID$_{var}$ | Clone$_{var}$ | Library Name | Nt$_H$ Alignment | Identity |
|---|---|---|---|---|---|
| 3 |    |             |           | 281–545   | 97% |
|   | 16 | 700718124H1 | MNBCNOT01 |           |     |
| 11|    |             |           | 362–626   | 97% |
| 3 |    |             |           | 1003–1259 | 96% |
|   | 17 | 700710954H1 | MNBFNOT02 |           |     |
| 11|    |             |           | 1084–1344 | 94% |
| 3 |    |             |           | 1081–1321 | 95% |
|   | 18 | 700707576H1 | MNBFNOT01 |           |     |
| 11|    |             |           | 1162–1390 | 91% |
| 3 |    |             |           | 228–392   | 97% |
|   | 19 | 700715158H1 | MNBCNOT01 |           |     |
| 11|    |             |           | 231–473   | 97% |
| 3 |    |             |           | 961–1083  | 87% |
|   | 20 | 700705541H1 | MNBFNOT01 |           |     |
| 11|    |             |           | 1042–1164 | 87% |
| 3 |    |             |           | 34–103    | 94% |
|   | 21 | 700719804H1 | MNBTNOT01 |           |     |
| 11|    |             |           | 158–226   | 94% |
| 3 |    |             |           | 502–1143  | 91% |
|   | 22 | 702769047H1 | CNLINOT01 |           |     |
| 11|    |             |           | 583–1224  | 91% |
| 3 |    |             |           | 376–1023  | 91% |
|   | 23 | 702763624H1 | CNLIUNN01 |           |     |
| 11|    |             |           | 457–1104  | 91% |
| 3 |    |             |           | 803–1230  | 91% |
|   | 24 | 702776664H1 | CNLINOT07 |           |     |
| 11|    |             |           | 884–1262  | 91% |
| 3 |    |             |           | 182–409   | 92% |
|   | 25 | 702778279H1 | CNLINOT07 |           |     |
| 11|    |             |           | 305–490   | 91% |
| 3 | 26 | 702249907H1 | CNBYNOT01 | 1511–1943 | 82% |
| 3 |    |             |           | 569–1173  | 90% |
|   | 27 | 702025443H1 | RABRTXT02 |           |     |
| 11|    |             |           | 650–1254  | 90% |
| 3 |    |             |           | 316–846   | 90% |
|   | 28 | 702028546H2 | RABRTXT02 |           |     |
| 11|    |             |           | 397–927   | 90% |
| 3 |    |             |           | 224–728   | 90% |
|   | 29 | 702160576H1 | RABRTXT10 |           |     |
| 11|    |             |           | 270–809   | 90% |
| 3 |    |             |           | 200–688   | 89% |
|   | 30 | 701938896H1 | RALIUNT18 |           |     |
| 11|    |             |           | 305–769   | 89% |
| 3 | 31 | 701646914H1 | RALITXT40 | 103–406   | 91% |

These cDNAs, SEQ ID NOS:16–31 are particularly useful for producing transgenic cell lines or organisms.

It will be appreciated by those skilled in the art that as a result of the degeneracy of the genetic code, a multitude of cDNAs encoding NRP, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotide encoding naturally occurring NRP, and all such variations are to be considered as being specifically disclosed.

The cDNAs of SEQ ID NOs:3–31 may be used in hybridization, amplification, and screening technologies to identify and distinguish among SEQ ID NO:3 or SEQ ID NO:11 and related molecules in a sample. The mammalian cDNAs may be used to produce transgenic cell lines or organisms which are model systems for human cancer, particularly cancers of the intestine, breast, uterus, liver, brain, and kidney and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention cDNA Libraries

In a particular embodiment disclosed herein, mRNA is isolated from mammalian cells and tissues using methods which are well known to those skilled in the art and used to prepare the cDNA libraries. The Incyte cDNAs were isolated from mammalian cDNA libraries a prepared as described in the EXAMPLES. The consensus sequences are chemically and/or electronically assembled from fragments including Incyte cDNAs and extension and/or shotgun sequences using computer programs such as PHRAP (P Green, University of Washington, Seattle Wash.), and AUTOASSEMBLER application (Applied Biosystems, Foster City Calif.). After verification of the 5' and 3' sequence, at least one representative cDNA which encodes NRP is designated a reagent.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (Applied Biosystems), the MEGABACE 1000 DNA sequencing system (APB), and the like. The sequences may be analyzed using a variety of algorithms well known in the art and described in Ausubel et al. (1997; Short Protocols in Molecular Biology, John Wiley & Sons, New York N.Y., unit 7.7) and in Meyers (1995; Molecular Biology and Biotechnology, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences, including vector or chimeric sequences, or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (Applied Biosystems), nested primers, and commercially available cDNA or genomic DNA libraries may be used to extend the nucleic acid sequence. For all PCR-based methods, primers may be designed using commercially available software, such as OLIGO primer analysis software (Molecular Biology Insights, Cascade Colo.) to be about 22 to 30 nucleotides in length, to have a GC content of about 50% or more, and to anneal to a target molecule at temperatures from about 55 C. to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the NRP, allelic variants, or related molecules. The probe may be DNA or RNA, may be single-stranded, and should have at least 50% sequence identity to any of the nucleic acid sequences, SEQ ID NOs:3–31. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. Hybridization can be performed at low stringency with buffers, such as 5×SSC with 1% sodium dodecyl sulfate (SDS) at 60 C., which permits the formation of a hybridization complex between nucleic acid sequences that contain some mismatches. Subsequent washes are performed at higher stringency with buffers such as 0.2×SSC with 0.1% SDS at either 45 C. (medium stringency) or 68 C. (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of detergents such as Sarkosyl or TRITON X-100 (Sigma- Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods well known in the art. Oligonucleotides or cDNAs may be used as hybridization probes or targets to monitor the expression level of large numbers of genes simultaneously or to identify genetic variants, mutations, and single nucleotide polymorphisms. Arrays may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to a particular chromosome, a specific region of a chromosome, or an artificial chromosome construction. Such constructions include human artificial chromosomes (HAC), yeast artificial chromosomes (YAC), bacterial artificial chromosomes (BAC), bacterial P1 constructions, or the cDNAs of libraries made from single chromosomes.

Expression

Any one of a multitude of cDNAs encoding NRP may be cloned into a vector and used to express the protein, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers may be propagated using culture techniques. Visible markers are also used to estimate the amount of protein expressed by the introduced genes. Verification that the host cell contains the desired cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6xHis, FLAG, MYC, and the like. GST and 6-His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N,N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431 A peptide synthesizer (Applied Biosystems). A protein or portion thereof may be substantially purified by preparative high performance liquid chromatography and its composition confirmed by amino acid analysis or by sequencing (Creighton (1984) *Proteins, Structures and Molecular Properties*, WH Freeman, New York N.Y.).

Preparation and Screening of Antibodies

Various hosts including goats, rabbits, rats, mice, humans, and others may be immunized by injection with NRP or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120)

Alternatively, techniques described for antibody production may be adapted, using methods known in the art, to produce epitope-specific, single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The NRP or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) Immunochemical Protocols, Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The cDNAs, fragments, oligonucleotides, complementary RNA and DNA molecules, and PNAs and may be used to detect and quantify differential gene expression for diagnosis of a disorder. Similarly antibodies which specifically bind NRP may be used to quantitate the protein. Disorders associated with differential expression include intestine cancer, breast cancer, uterine cancer, liver cancer, brain cancer, and kidney cancer. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies or in clinical trials or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Proto-* cols in *Immunology*, Wiley-Interscience, New York N.Y.; and Pound, supra.)

Therapeutics

Chemical and structural similarity, in particular the alpha-beta hydrolase fold and the androgen receptor signatures, exists between regions of NRP1 (2227688; SEQ ID NO:1), NRP2 (3507515; SEQ ID NO:2), mouse Ndr2 (g6141566; SEQ ID NO:32), and human RTP (g1596167; SEQ ID NO:33) as shown in FIGS. 3A, 3B, and 3C. In addition, differential expression is associated with cancer, particularly cancers of the intestine, breast, uterus, liver, brain, and kidney as shown in Tables 1 and 2. NRP clearly plays a role in cancer, particularly cancers of the intestine, breast, uterus, liver, brain, and kidney.

In the treatment of conditions associated with increased expression of NRP, it is desirable to decrease expression or protein activity. In one embodiment, the an inhibitor, antagonist or antibody of the protein may be administered to a subject to treat a condition associated with increased expression or activity. In another embodiment, a pharmaceutical composition comprising an inhibitor, antagonist or antibody in conjunction with a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

In the treatment of conditions associated with decreased expression of NRP, it is desirable to increase expression or protein activity. In one embodiment, the protein, an agonist or enhancer may be administered to a subject to treat a condition associated with decreased expression or activity. In another embodiment, a pharmaceutical composition comprising the protein, an agonist or enhancer in conjunction with a pharmaceutical carrier may be administered to a subject to treat a condition associated with the decreased expression or activity of the endogenous protein. In an additional embodiment, a vector expressing cDNA may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding NRP. Oligonucleotides designed to inhibit transcription initiation are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2'O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The cDNA encoding NRP may be used to screen a library of molecules or compounds for specific binding affinity. The libraries may be aptamers, DNA molecules, RNA molecules, PNAs, peptides, proteins such as transcription factors, enhancers, repressors, and other ligands which regulate the activity, replication, transcription, or translation of the endogenous gene. The assay involves combining a polynucleotide with a library of molecules under conditions allowing specific binding, and detecting specific binding to identify at least one molecule which specifically binds the single-stranded or double-stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment, the protein or a portion thereof may be used to purify a ligand from a sample. A method for using a protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, NRP may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands, and the specificity of binding or formation of complexes between the expressed protein and the ligand may be measured. Specific binding between the protein and molecule may be measured. Depending on the particular kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. Nos. 5,175,383 and 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. The preparation of the human SEMVNOT01 seminal vesicle library will be described.

I cDNA Library Construction

The SEMVNOT01 cDNA library was constructed from microscopically normal seminal vesicles removed from a 58-year-old Caucasian male (specimen #0759B). Pathology for the associated tumor tissue indicated adenocarcinoma of the prostate, Gleason grade 3+2. The frozen tissue was homogenized and lysed using a POLYTRON homogenizer (Brinkmann Instruments, Westbury N.J.) in guanidinium isothiocyanate solution. The lysate was centrifuged over a 5.7 M CsCl cushion using an SW28 rotor in an L8-70M ultracentrifuge (Beckman Coulter, Fullerton Calif.) for 18 hours at 25,000 rpm at ambient temperature. The RNA was extracted with acid phenol, pH 4.7, precipitated using 0.3 M sodium acetate and 2.5 volumes of ethanol, resuspended in RNAse-free water, and treated with DNAse at 37 C. The RNA was reextracted and precipitated as before. The mRNA was isolated with the OLIGOTEX kit (Qiagen, Chatsworth Calif.) and used to construct the cDNA library.

The mRNA was handled according to the recommended protocols in the SUPERSCRIPT plasmid system (Life Technologies) which contains a NotI primer-adaptor designed to prime the first strand cDNA synthesis at the poly(A) tail of mRNAs. Double stranded cDNA was blunted, ligated to EcoRI adaptors and digested with NotI (New England Biolabs, Beverly Mass.). The cDNAs were fractionated on a SEPHAROSE CL4B column (APB), and those cDNAs exceeding 400 bp were ligated into pINCY plasmid (Incyte Genomics). The plasmid pINCY was subsequently transformed into DH5α competent cells (Life Technologies).

II Construction of pINCY Plasmid

The plasmid was constructed by digesting the PSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid, pSPORT I-ΔRI, which showed no digestion with EcoRI, was digested with Hind III (New England Biolabs); and the overhanging ends were filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP kit (Edge Biosystems, Gaithersburg Md.) or the REAL PREP 96 plasmid kit (Qiagen). A kit consists of a 96-well block with reagents for 960 purifications. The recommended protocol was employed except for the following changes: 1) the bacteria were cultured in 1 ml of sterile TERRIFC BROTH (APB) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (Applied Biosystems) or the MEGABACE 1000 DNA sequencing system (APB). Most of the isolates were sequenced according to standard ABI protocols and kits (Applied Biosystems) with solution volumes of 0.25×–1.0× concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using commercially available primer analysis software to be about 22 to 30 nucleotides in length, to have a GC content of about 50% or more, and to anneal to the target sequence at temperatures of about 68 C. to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C., three min; Step 2: 94 C., 15 sec; Step 3: 60 C., one min; Step 4: 68 C., two min; Step 5: Steps 2, 3, and 4 repeated 20 times; Step 6: 68 C., five min; Step 7: storage at 4 C. In the alternative, the parameters for primer pair T7 and SK+ (Stratagene) were as follows: Step 1: 94 C., three min; Step 2: 94 C., 15 sec; Step 3: 57 C., one min; Step 4: 68 C., two min; Step 5: Steps 2, 3, and 4 repeated 20 times; Step 6: 68 C., five min; Step 7: storage at 4 C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose minigel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37 C. in 384-well plates in LB/2×carbenicillin liquid media.

The cells were lysed, and DNA was amplified using primers, Taq DNA polymerase (APB) and Pfu DNA polymerase (Stratagene) with the following parameters: Step 1: 94 C., three min; Step 2: 94 C., 15 sec; Step 3: 60 C., one min; Step 4: 72 C., two min; Step 5: steps 2, 3, and 4 repeated 29 times; Step 6: 72 C., five min; Step 7: storage at 4 C. DNA was quantified using PICOGREEN quantitation reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (Applied Biosystems).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST2 to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (sura), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the stringency for an exact match was set from a lower limit of about 40 (with 1–2% error due to uncalled bases) to a 100% match of about 70.

The BLAST software suite (NCBI, Bethesda Md.; http://www.ncbi.nlm.nih.gov/gorf/b12.html), includes various sequence analysis programs including "blastn" that is used to align nucleotide sequences and BLAST2 that is used for direct pairwise comparison of either nucleotide or amino acid sequences. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap x drop-off: 50; Expect: 10; Word Size: 11; and Filter: on. Identity is measured over the entire length of a sequence. Brenner et al. (1998; Proc Natl Acad Sci 95:6073–6078, incorporated herein by reference) analyzed BLAST for its ability to identify structural homologs by sequence identity and found 30% identity is a reliable threshold for sequence alignments of at least 150 residues and 40%, for alignments of at least 70 residues.

The cDNAs of this application were compared with assembled consensus sequences or templates found in the LIFESEQ GOLD database (Incyte Genomics). Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another, and those having local similarity of at least 82% were combined and reassembled. Bins having templates with less than 95% local identity were split. Templates were subjected to analysis by STITCHER/EXON MAPPER algorithms that determine the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1\times 10^{-8}$. The templates were also subjected to frameshift FASTx against GENPEPT, and homolog match was defined as having an E-value of $\leq 1\times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No.08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.; http://pfam.wustl.edu/). The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNA encoding NRP that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 100 C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 μl TE buffer, denaturing by heating to 100 C. for five min, and briefly centrifuging. The denatured cDNA is then added to a REDIPRIME tube (APB), gently mixed until blue color is evenly distributed, and briefly centrifuged. Five μl of [$^{32}$P]dCTP is added to the tube, and the contents are incubated at 37 C. for 10 min. The labeling reaction is stopped by adding 5 μl of 0.2M EDTA, and probe is purified from unincorporated nucleotides using a PROBEQUANT G-50 microcolumn (APB). The purified probe is heated to 100 C. for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 μl TE buffer and adding 5 μl 5×buffer, 1 μl 0.1 M DTT, 3 μl Cy3 or Cy5 labeling mix, 1 μl RNase inhibitor, 1 μl reverse transcriptase, 5 μl 1×and yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C. for two hr. The reaction mixture is then incubated for 20 min at 85 C., and probes are purified using two successive CHROMA SPIN+TE 30 columns (Clontech, Palo Alto Calif.). Purified probe is ethanol precipitated by diluting probe to 90 μl in DEPC-treated water, adding 2 μl 1 mg/ml glycogen, 60 μl 5 M sodium acetate, and 300 μl 100% ethanol. The probe is centrifuged for 20 min at 20,800×g, and the pellet is resuspended in 12 μl resuspension buffer, heated to 65 C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M Na$_2$HPO$_4$, 5 mM EDTA, pH 7) at 55 C. for two hr. The probe, diluted in 15 ml fresh hybridization solution, is then added to the membrane. The membrane is hybridized with the probe at 55 C. for 16 hr. Following hybridization, the membrane is washed for 15 min at 25 C. in 1 mM Tris (pH 8.0), 1% Sarkosyl, and four times for 15 min each at 25 C. in 1 mM Tris (pH 8.0). To detect hybridization complexes, XOMAT-AR film (Eastman Kodak, Rochester N.Y.) is exposed to the membrane overnight at −70 C., developed, and examined visually.

Polymer Coated Slide-based Hybridization

Probe is heated to 65 C. for five min, centrifuged five min at 9400 rpm in a 5415C microcentrifuge (Eppendorf Scientific, Westbury N.Y.), and then 18 μl is aliquoted onto the array surface and covered with a coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hr at 60 C. The arrays are washed for 10 min at 45 C. in 1×SSC, 0.1% SDS, and three times for 10 min each at 45 C. in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20X microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cyγ. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis was performed at a product score of 70 and is shown in Tables 1 and 2. All sequences and cDNA libraries in the LIFESEQ database were categorized by system, organ/tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

IX Complementary Molecules

Molecules complementary to the cDNA, from about 5 (PNA) to about 5000 bp (complement of a cDNA insert), are used to detect or inhibit gene expression. Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the protein.

X Expression of NRP

Expression and purification of the protein are achieved using either a mammalian cell expression system or an insect cell expression system. The pUB6/y5-His vector system (Invitrogen, Carlsbad Calif.) is used to express NRP in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6xHis) sequence for rapid purification on PROBOND resin (Invitrogen). Transformed cells are selected on media containing blasticidin.

Spodoptera frugiperda (Sf9) insect cells are infected with recombinant Autographica californica nuclear polyhedrosis virus (baculovirus). The polyhedrin gene is replaced with the cDNA by homologous recombination and the polyhedrin promoter drives cDNA transcription. The protein is synthesized as a fusion protein with 6xhis which enables purification as described above. Purified protein is used in the following activity and to make antibodies.

XI Production of Antibodies

NRP is purified using polyacrylamide gel electrophoresis and used to immunize mice or rabbits. Antibodies are produced using the protocols below. Alternatively, the amino acid sequence of NRP is analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocldng with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FITC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C. until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-GaL Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-GaV/-Trp/-Ura, and white colonies are isolated and propagated. The pB42AD-cDNA plasmid, which contains a cDNA encoding a protein that physically interacts with the protein, is isolated from the yeast cells and characterized.

XV NRP Assay

Assays of transcriptional regulation of NRP are performed in human carcinoma cell lines as described by Ulrix et al. (sura). NRP expression is monitored in the presence and absence of androgens, retinoic acid, homocysteine, or nickel compounds. Total RNA is determined by Northern blot analysis.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1

| Tissue Category | Clone Count | Found in | Abs Abund | Pct Abund |
| --- | --- | --- | --- | --- |
| Cardiovascular System | 266190 | 11/68 | 20 | 0.0075 |
| Connective Tissue | 144645 | 3/47 | 5 | 0.0035 |
| Digestive System | 501101 | 20/148 | 22 | 0.0044 |
| Embryonic Structures | 106713 | 2/21 | 2 | 0.0019 |
| Endocrine System | 225386 | 11/53 | 26 | 0.0115 |
| Exocrine Glands | 254635 | 22/64 | 31 | 0.0122 |
| Reproductive, Female | 427284 | 25/106 | 39 | 0.0091 |
| Reproductive, Male | 448207 | 21/114 | 34 | 0.0076 |
| Germ Cells | 38282 | 1/5 | 3 | 0.0078 |
| Hemic and Immune System | 680277 | 9/159 | 20 | 0.0029 |
| Liver | 109378 | 4/35 | 9 | 0.0082 |
| Musculoskeletal System | 159280 | 14/47 | 21 | 0.0132 |
| Nervous System | 955753 | 108/198 | 277 | 0.0290 |
| Pancreas | 110207 | 1/24 | 2 | 0.0018 |
| Respiratory System | 390086 | 11/93 | 17 | 0.0044 |
| Sense Organs | 19256 | 2/8 | 7 | 0.0364 |
| Skin | 72292 | 1/15 | 2 | 0.0028 |
| Stomatognathic System | 12923 | 3/10 | 4 | 0.0310 |
| Unclassified/Mixed | 120926 | 2/13 | 6 | 0.0050 |
| Urinary Tract | 279062 | 13/64 | 16 | 0.0057 |
| Totals | 5321883 | 284/1292 | 563 | 0.0001 |

TABLE 2

| Library ID | Clone Count | Library Description | Abs Abund | Pct Abund |
| --- | --- | --- | --- | --- |
| SINTTUT01 | 2596 | sm intestine tumor, ileum, carcinoid, 42M | 2 | 0.0770 |
| BRSTTUP03 | 831 | breast tumor, ductal, poorly differentiated, F, 3' CGAP | 2 | 0.2407 |
| BRSTTUT17 | 2698 | breast tumor, ductal CA, 65F | 1 | 0.0371 |
| UTRSTUE01 | 3545 | uterus tumor, leiomyoma, 37F, 5RP | 3 | 0.0846 |
| LIVRTUT04 | 3640 | liver tumor, hepatoma, 50M | 3 | 0.0824 |
| BRAITUP04 | 633 | brain tumor, oligodendroglioma, 44M, WN | 4 | 0.6319 |
| BRAITUP06 | 410 | brain tumor, astrocytoma, 44M, WN | 1 | 0.2439 |

TABLE 2-continued

| Library ID | Clone Count | Library Description | Abs Abund | Pct Abund |
|---|---|---|---|---|
| KIDNTUT13 | 3776 | kidney tumor, renal cell CA, 51F | 2 | 0.0530 |
| KIDNTUP05 | 2352 | kidney tumor, renal cell, 3' CGAP | 1 | 0.0425 |
| KIDNTUE01 | 2906 | kidney tumor, renal cell CA, 46M, 5RP | 1 | 0.0344 |

What is claimed is:

1. An isolated cDNA comprising a nucleic acid sequence encoding a protein selected from the amino acid sequence of SEQ ID NO:1 and SEQ ID NO:2, or the complement thereof.

2. An isolated cDNA comprising a nucleic acid sequence selected from:
   a) SEQ ID NO:3 and SEQ ID NO:11 or the complement thereof;
   b) a fragment of SEQ ID NO:3 selected from SEQ ID NOs:4–10 or the complement thereof;
   c) a fragment of SEQ ID NO:11 selected from SEQ ID NOs: 12–15 or the complement thereof; and
   d) a variant of SEQ ID NO:3 or SEQ ID NO:11 selected from SEQ ID NOs:16–31 or the complement thereof.

3. An isolated cDNA comprising the nucleic acid sequence of SEQ ID NO:3.

4. An isolated cDNA comprising the nucleic acid sequence of SEQ ID NO:11.

5. A composition comprising the cDNA or the complement of the cDNA of claim 1 and a labeling moiety.

6. A vector comprising the cDNA of claim 1.

7. A host cell comprising the vector of claim 6.

8. A method for using a cDNA to produce a protein, the method comprising:
   a) culturing the host cell of claim 7 under conditions for protein expression; and b) recovering the protein from the host cell culture.

9. A method for using a cDNA to detect expression of a nucleic acid in a sample comprising:
   a) hybridizing the composition of claim 5 to nucleic acids of the sample, thereby forming hybridization complexes; and
   b) comparing hybridization complex formation with a standard, wherein the comparison indicates expression of the cDNA in the sample.

10. The method of claim 9 further comprising amplifying the nucleic acids of the sample prior to hybridization.

11. The method of claim 9 wherein the composition is attached to a substrate.

12. The method of claim 9 wherein the cDNA is differentially expressed when compared with a standard and is diagnostic of a cancer, particularly intestine cancer, breast cancer, uterine cancer, liver cancer, brain cancer, and kidney cancer.

13. A method of using a cDNA to screen a plurality of molecules or compounds, the method comprising:
   a) combining the cDNA of claim 1 with a plurality of molecules or compounds under conditions to allow specific binding; and
   b) detecting specific binding, thereby identifying a molecule or compound which specifically binds the cDNA.

14. The method of claim 13 wherein the molecules or compounds are selected from DNA molecules, RNA molecules, peptide nucleic acids, artificial chromosome constructions, peptides, transcription factors, repressors, and regulatory molecules.

* * * * *